(12) United States Patent
Wirthlin et al.

(10) Patent No.: US 8,934,102 B2
(45) Date of Patent: Jan. 13, 2015

(54) SYSTEM AND METHOD FOR DETERMINING FLUID PARAMETERS

(71) Applicant: Intellectual Reserves, LLC, Parker, TX (US)

(72) Inventors: Alvin R Wirthlin, Frisco, TX (US); Leon Brown, Parker, TX (US)

(73) Assignee: Intellectual Reserves, LLC, Parker, TX (US)

( * ) Notice: Subject to any disclaimer, the term of this patent is extended or adjusted under 35 U.S.C. 154(b) by 0 days.

(21) Appl. No.: 14/300,431

(22) Filed: Jun. 10, 2014

(65) Prior Publication Data

US 2014/0368823 A1    Dec. 18, 2014

Related U.S. Application Data

(60) Provisional application No. 61/836,062, filed on Jun. 17, 2013.

(51) Int. Cl.
*G01N 21/41* (2006.01)
*G01N 21/55* (2014.01)

(52) U.S. Cl.
CPC ....................................... *G01N 21/55* (2013.01)
USPC .......................................... 356/448; 356/135

(58) Field of Classification Search
CPC .............................. G01N 21/41; G01N 21/55
USPC ................. 356/448, 128, 130, 134, 135, 136
See application file for complete search history.

(56) References Cited

U.S. PATENT DOCUMENTS

| | | | | |
|---|---|---|---|---|
| 3,449,051 A * | 6/1969 | Levitt | ............................ | 356/130 |
| 4,544,255 A * | 10/1985 | Utagawa | ....................... | 396/114 |
| 4,962,746 A * | 10/1990 | Miyata et al. | ................. | 123/613 |
| 5,046,842 A * | 9/1991 | Miyata et al. | ................. | 356/136 |
| 5,048,952 A * | 9/1991 | Miyata et al. | ................. | 356/135 |
| 5,969,808 A * | 10/1999 | Cotton et al. | ................. | 356/135 |
| 6,172,746 B1 * | 1/2001 | Byrne et al. | .................. | 356/135 |
| 7,492,447 B2 * | 2/2009 | Nakajima et al. | ............. | 356/128 |
| 8,542,353 B2 * | 9/2013 | Christian et al. | .............. | 356/128 |
| 2009/0015822 A1 * | 1/2009 | Uchida et al. | ................. | 356/135 |

* cited by examiner

*Primary Examiner* — Roy M Punnoose
(74) *Attorney, Agent, or Firm* — Alvin R. Wirthlin

(57) ABSTRACT

A system and method for measuring the quality of a fluid includes an optical body forming a measurement surface configured for contacting the fluid to be measured; a light source for projecting radiant energy into the optical body and toward the measurement surface at a predetermined angle; an optical sensor module arranged for detecting an image of at least reflected radiant energy from the measurement surface, the optical sensor module includes a two-dimensional array of light sensors or pixels, each pixel having a plurality of brightness levels; and a processor for setting a brightness threshold value, comparing the threshold value to the brightness level of each pixel, and counting the number of pixels above and/or below the brightness threshold value.

20 Claims, 17 Drawing Sheets

REFLECTION DATA

| Medium | 4-Burst Ave. (4 x 8 Lines) | 8-Line Ave. Deviation | Delta |
|---|---|---|---|
| De-ionized Water | 46,465 | +24 -51 | |
| | | | Δ = 34,257 |
| 30.0% DEF | 16,208 | +71 -144 | |
| | | | Δ = 5,351 |
| 32.0% DEF | 10,857 | +40 -54 | |
| | | | Δ = 1,278 |
| 33.9% DEF | 9,581 | +12 -11 | |

*FIG. 6*

COMBINED REFLECTION AND REFRACTION DATA

| Medium | 4-Burst Ave. (4 x 8 Lines) | 8-Line Ave. Deviation | Delta |
|---|---|---|---|
| De-ionized Water | 51,131 | +29 -29 | |
| 30.0% DEF | 25,688 | +47 -73 | Δ = 25,443 |
| 32.0% DEF | 17,719 | +36 -28 | Δ = 7,969 |
| 33.9% DEF | 9,019 | +52 -16 | Δ = 8,700 |

*FIG. 9*

SYSTEM AND METHOD FOR DETERMINING FLUID PARAMETERS

CROSS-REFERENCE TO RELATED APPLICATIONS

This application claims the benefit of U.S. Provisional Application No. 61/836,062 filed on Jun. 17, 2013.

BACKGROUND OF THE INVENTION

This invention relates to measurement devices, and more particularly to a system and method for determining the quality and other parameters of fluids.

Transducers for measuring liquid level and other parameters are often used in vehicles, industrial equipment and other systems and components. The electrical output of such transducers change in response to a change in the liquid being measured, and is typically in the form of a change in resistance, capacitance, current flow, magnetic field, frequency, and so on. These types of transducers may include variable capacitors or resistors, optical components, Hall Effect sensors, strain gauges, ultrasonic devices, and so on.

In vehicles, industrial equipment and other systems powered by diesel fuel, a Selective Catalytic Reduction (SCR) system has been used to inject urea—a liquid-reductant agent—through a catalyst into the exhaust stream of a diesel engine. Urea sets off a chemical reaction that converts nitrogen oxides in the exhaust into nitrogen and water, which is then harmlessly expelled through the vehicle tailpipe. Previous urea quality sensor solutions have attempted to address industry quality control by ensuring that a specific quality of urea can be delivered into the exhaust gas stream. If the engine is operated without urea solution in the onboard urea tank, excessive NOx emissions can occur. Using a urea quality sensor, the SCR system can monitor the contents of the urea tank to alert an operator and/or system that the urea tank has been filled with other fluids, e.g., with tap water, coolant, windshield wiper fluid, oil, incorrect concentrations of urea solutions, and so on, instead of the correct concentration of urea solution. The introduction of a urea quality sensor into the SCR system also reduces the risk of tampering or accidental mis-filling and helps ensure compliance to environmental legislation, thus satisfying concerns of users and legislators alike. The urea quality sensor is intended to contribute to the overall success of SCR as a NOx reduction technology. However, prior art solutions for measuring the presence or absence of the required urea concentration, such as refractive index measurements, capacitive, acoustic, and other known techniques, have been unable to measure the urea concentration with any degree of suitable accuracy to meet rigid industry and legislative requirements.

It would therefore be desirous to provide a system and method for determining the quality of fluids and other parameters with a higher degree of accuracy than prior art systems and methods in order to quantify whether or not proper fluid and/or the proper concentrations of fluids are being used in vehicles, machinery, and so on.

BRIEF SUMMARY OF THE INVENTION

According to one aspect of the invention, a system for measuring one or more parameters of a fluid includes: an optical body having a measurement surface configured for contacting the fluid to be measured; a light source for projecting radiant energy toward the measurement surface at a predetermined angle; an optical sensor module arranged for detecting an image of at least reflected radiant energy from the measurement surface, the optical sensor module including a two-dimensional array of light sensors, each light sensor being capable of detecting a plurality of brightness levels; and a processor configured for setting a brightness threshold value and comparing the brightness threshold value to the brightness level of at least some of the light sensors. In this manner, the at least one parameter of the fluid is determined at least in part by counting the light sensors above and/or below the brightness threshold value.

According to a further aspect of the invention, an optical body for measuring one or more parameters of a fluid comprises: a top surface adapted to receiving a light source; a measurement surface extending from the top surface for contacting the fluid to be measured; a bottom surface extending from the measurement surface at a predetermined angle, the bottom surface being adapted to receiving a digital image sensor array; left and right side surfaces extending between the top, measurement and bottom surfaces; and a plurality of openings extending through the optical body between the left and right side surfaces, the openings being strategically placed to divide the light source into at least a measurement component of light and a reference component of light, with the measurement component of light projecting toward the measurement surface at a predetermined angle to be reflected and/or refracted therefrom towards a first sensor area of the optical sensor module, and the reference component of light projecting towards the bottom surface and a second sensor area of the optical sensor module.

According to yet a further aspect of the invention, a method of determining at least one parameter of a fluid to be measured comprises: providing an optical measurement surface for contacting the fluid to be measured; directing radiant energy toward the optical measurement surface at a predetermined angle such that at least a portion of the radiant energy is reflected and/or refracted off of the optical measurement surface; detecting a two-dimensional image of the reflected and/or refracted radiant energy from the measurement surface with a two-dimensional array of light sensors, each light sensor being capable of detecting a plurality of brightness levels of the reflected and/or refracted radiant energy; setting a brightness threshold value for at least some of the light sensors; and adding the light sensors above and/or below the brightness threshold value to thereby determine the at least one parameter of the fluid.

BRIEF DESCRIPTION OF THE DRAWINGS

The foregoing summary as well as the following detailed description of the preferred embodiments of the present invention will be best understood when considered in conjunction with the accompanying drawings, wherein:

FIG. 6 is a chart showing sensor data obtained during an actual measurement of different fluids and different concentrations of fluids;

FIG. 9 is a chart showing sensor data obtained during an actual measurement of different fluids and different concentrations of fluids with the system of the second embodiment as depicted in FIG. 4;

It is noted that the drawings are intended to depict only typical embodiments of the invention and therefore should not be considered as limiting the scope thereof. It is further noted that the drawings are not necessarily to scale. The invention will now be described in greater detail with reference to the accompanying drawings, wherein like designations denote like elements throughout the drawings.

DETAILED DESCRIPTION OF THE INVENTION

Figure 1:
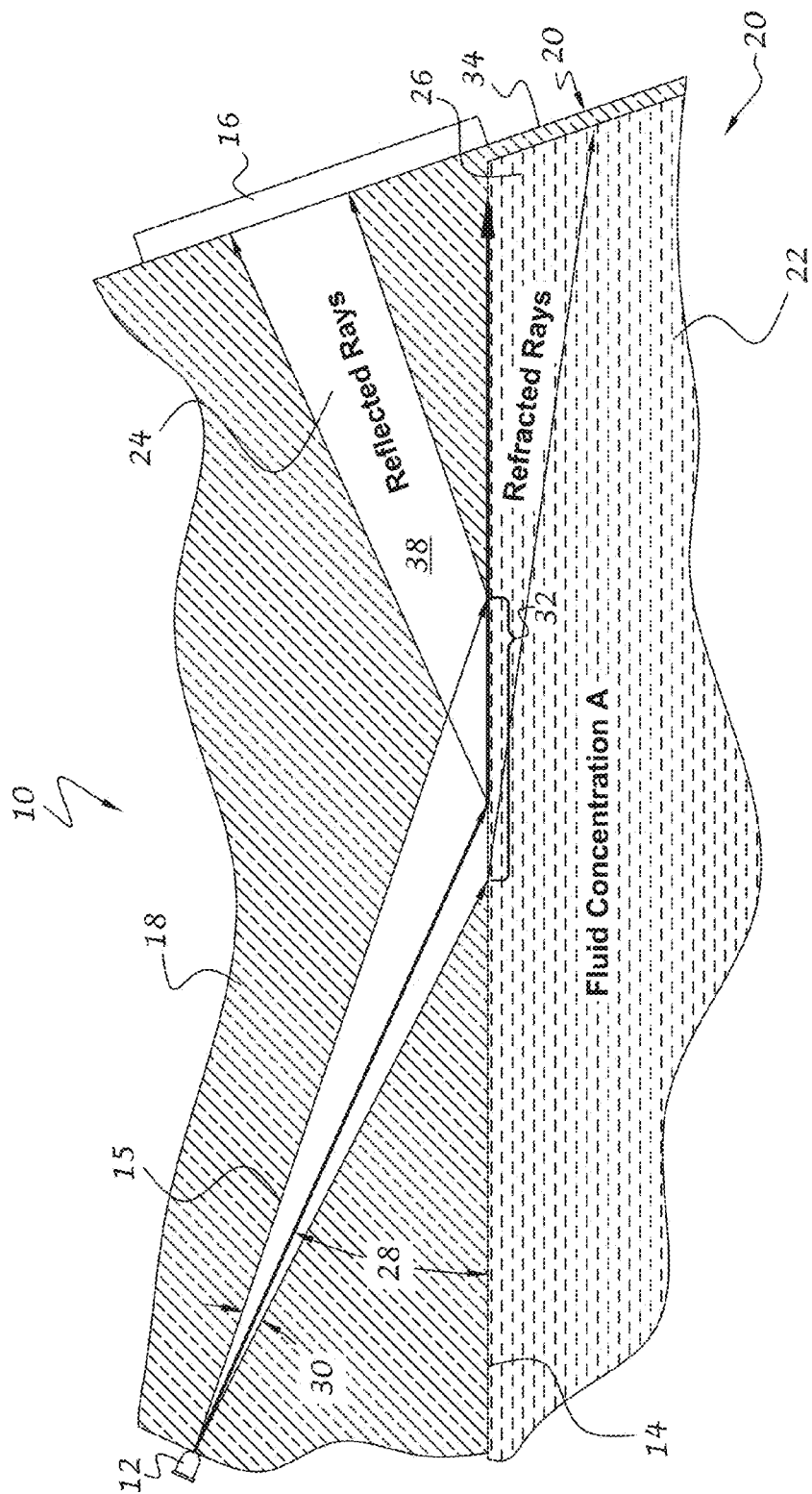
FIG. 1 is a diagrammatic view of a measurement system in accordance with the present invention when measuring the quality or other parameter(s) of a first fluid.

Referring to the drawings, and to FIG. 1 particular, a system 10 for measuring the quality of a fluid or solution, as well as other parameters, in accordance with the present invention is illustrated. Parameters that can be measured by the invention include, but are not limited to, the purity of a fluid or solution, the percentage or ratios of different fluids and/or solids within a solution, the refractive index of fluids, solutions, and/or solids, the absorption characteristics of fluids, solutions, and/or solids, the density of fluids and solutions, combinations thereof, and so on.

The system 10 preferably includes a light source 12 positioned for projecting radiant energy 15 through an optical body 18, a measurement surface 14 that abuts a reservoir 20 for holding a quantity of fluid 22, and an optical sensor module 16 having a two-dimensional array of sensors for capturing reflected rays 24 and/or refracted rays 26 from the light source 12. Although the present invention will be described with particular exemplary examples and data relating to the measurement or determination of a standardized aqueous urea solution comprising 32.5% high purity urea and 67.5% deionized water and variations thereof (often referred to as diesel exhaust fluid (DEF) or AdBlue), it will be understood that one or more parameters of virtually any fluid, combinations of fluids, solutions, semi-solids, and even solids can be measured with the fluid measuring systems as described herein without departing from the spirit and scope of the invention.

In accordance with an exemplary embodiment of the invention, the light source 12 is positioned for projecting the radiant energy 15 at a particular angle 28 with respect to the measurement surface 14. The particular angle 28 is largely dependent on the optical properties of the fluid being measured, such as the refractive index of the fluid. In accordance with one embodiment of the invention, where the ideal fluid 22 being measured is 32.5% laboratory grade urea in deionized water, the particular angle 28 is approximately equal to the critical angle (or the converse of the critical angle) as determined by a ratio of the refractive indices of the optical body 18 and the fluid 22. In addition, the light source 12 also projects radiant energy 15 at a cone angle 30 so that the radiant energy is distributed over a relatively large surface area 32 so that rays of light extend at angles less than, equal to, and greater than the critical angle (or converse to the critical angle). In this manner, a wide variety of different fluids, fluid combinations, solutions, semi-solids, and solids with different refractive indices can be measured.

The optical sensor module 16 is preferably in the form of a two-dimensional image sensor, such as a digital image module. The digital image module is preferably of a low-cost variety, having a particular number of pixels or independent sensors, commonly used in other mass-produced applications such as smart devices, mobile phones, touch pads, digital cameras, and so on. Under present market conditions, the sheer number of such modules produced in mass quantity can be taken advantage of in accordance with one aspect of the invention to produce a relatively low-cost measurement transducer with relatively high accuracy with respect to prior art solutions. A suitable image module may include, but is not limited to, a CMOS image sensor with a predetermined array of light sensitive sensors or pixels to capture either a virtual image of the surface area 32 either at the noted location or as projected on a diffuse surface 34 of the optical body 18 associated with the sensor 16. With this arrangement, lenses, mirrors, and/or other optical components are not needed, thus significantly reducing the number of parts, assembly time and other manufacturing costs, as well as their associated drawbacks (such as condensation, parallax errors, inherent defects in low-cost lenses, lens systems, mirrors, and so on). However, it will be understood that real image data can be captured and processed using one or more lenses and/or lens systems, mirrors, and other optical elements without departing from the spirit and scope of the invention. Regardless of the manner in which the image data is created (e.g. either real or virtual image creation), it will be understood that the image data can be processed in a similar manner to determine the fluid quality, as will be described in greater detail below with reference to FIGS. 5 and 15.

In accordance with an exemplary embodiment of the invention, an 8-bit CMOS monochrome digital image sensor chip was used to collect the data as shown in FIGS. 6, 7, 9, and 10 to measure and compare the parameters of different fluids. The exemplary digital image sensor has a resolution of 640 by 480 pixels (a matrix of 307,200 pixels), with each pixel capable of distinguishing and capturing 256 levels of visible light. It was found that such a module is suitable for capturing image data of the fluid to be measured, including subtle differences in fluid composition, to a relatively high degree of resolution. Accordingly, relatively high accuracy measurements have been obtained for determining the quality and/or type of the liquid being measured when compared with prior art solutions, as will be described in greater detail below. The digital image sensor chip is capable of operation at 15 frames per second (fps) or more in full resolution. The data captured during imaging can be transferred by any available data format such as a standard parallel digital video port (DVP) or by a single-lane MIPI high-speed serial interface with RAW pixel data, RGB, YUV, and/or Compressed Data outputs.

It will be understood that other image sensors with more or less resolution, color and/or black and white capabilities, as well as other image sensing technologies, such as charge-coupled devices (CCD's), multiple linear arrays, and so on, can be used without departing from the spirit and scope of the invention.

The light source 12 preferably comprises a light emitting diode (LED), and both the light source and image module 16 can be surface-mount devices to efficiently optically couple the devices to the optical body 18. A shield 36 (FIG. 3) or other light blocking member can be provided between the image module 16 and the light source 12 to prevent the direct transmission of stray light from the light source to the image module. It will be understood that other light sources can be used, such as, without limitation, incandescent bulbs, laser diodes, or any other source that emits radiant energy in one or more of the visible, ultra-violet, or infra-red spectrums. It will be further understood that other photosensors can be used, such as, without limitation, photocells, photodiodes, and photoconductors.

It will be further understood that the position of the light source and image module may be reversed or located at other positions without departing from the spirit and scope of the invention. In addition, the light source and/or the image module can be remotely located from the optical body 18 through the use of intermediate members such as optical fibers, transparent image conducting rods or fibers, lenses, or other suitable light guides.

Figure 2:
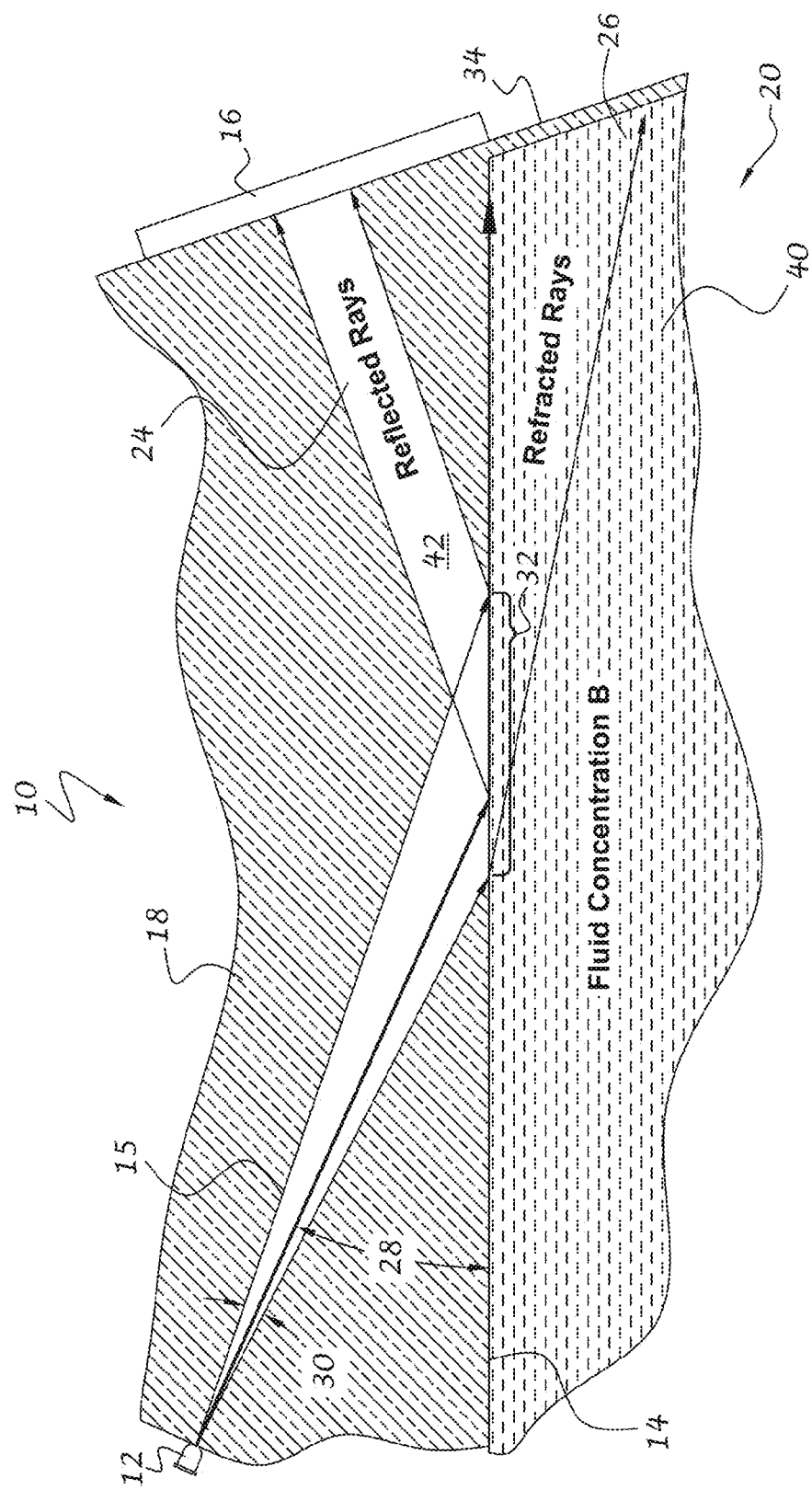
FIG. 2 is a view similar to FIG. 1 when measuring the quality or other parameter(s) of a second fluid different from the first fluid.

In use, as shown in FIG. 1, for a first fluid 22, the reflected rays 24 are directed towards the optical sensor module 16. Because of the refractive index of the fluid 22 and the refractive index of the optical body 18, a particular area 38 of reflected rays will be present. In contrast, as shown in FIG. 2, the area 42 of reflected rays is smaller than the area 38 of FIG. 1, due to the difference in the refractive index of the fluid 40. Accordingly, an area of the optical sensor module 16 exposed to the reflected rays will change from fluid to fluid. Since the sensed areas for each fluid is different, the optical sensor module 16 will output different signals which can be processed to determine whether or not the liquid being measured falls within acceptable parameters.

Figure 3:
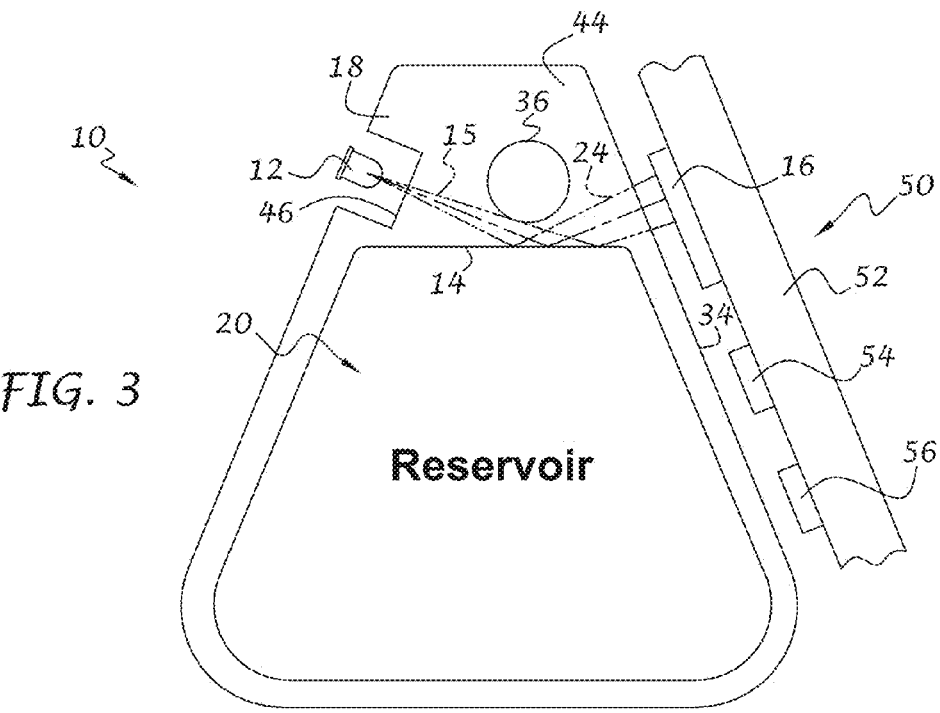
FIG. 3 is a top plan view of an exemplary measurement transducer assembly implementing the system of FIGS. 1 and 2 and including a sensor array in accordance with the invention.
Figure 4:
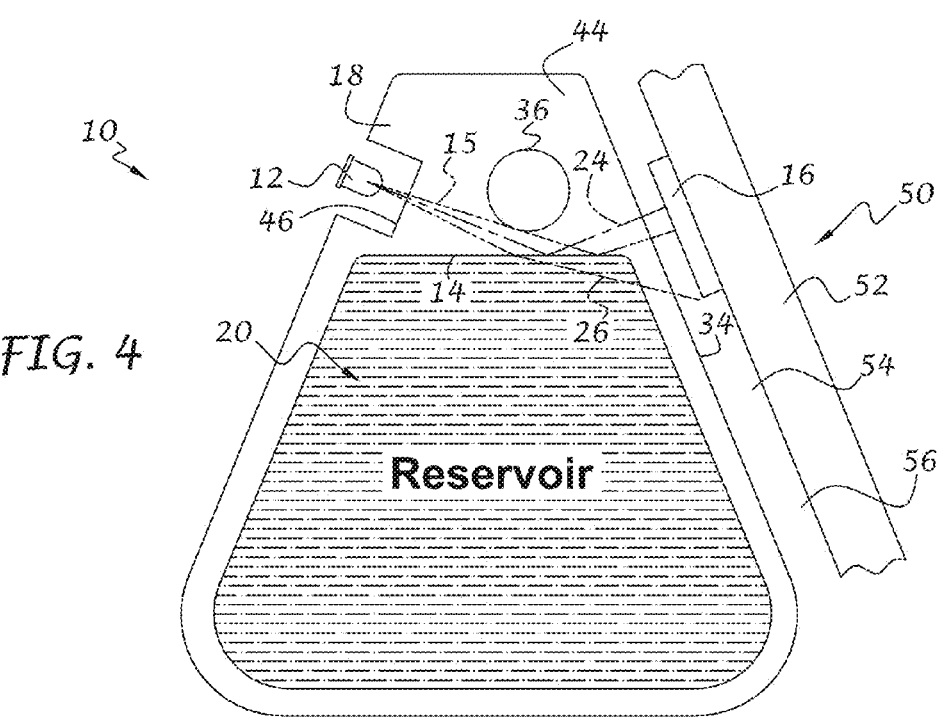
FIG. 4 is a top plan view of an exemplary measurement transducer assembly in accordance with a further embodiment of the invention showing a sensor array shifted to collected both reflection and refraction (absorption) data of different fluids, semi-solids or solids.

Turning now to FIGS. 3 and 4, the system 10 includes a measurement housing 44, given by way of example only, that incorporates the optical body 18 and includes the reservoir 20 for receiving the fluid to be measured, the measurement surface 14, the image surface 34 associated with the sensor 16, an aperture surface 46 associated with the light source 12, and a light blocking opening 36 positioned between the aperture surface 46 and the image surface 34. The image surface 34 can include a roughened surface, a lens material, or other surface conducive of forming an image from the reflected and/or refracted light associated with the measurement surface 14. In this manner, the need for one or more lenses is eliminated, thus reducing system costs and allowing the construction of a more compact measuring unit. Likewise, the aperture surface 46 preferably includes a small opening to permit radiant energy from the light source 12 to project therethrough at a particular cone angle. In this manner, a low-cost surface-mount LED or the like can be used without the need for focusing lenses or the like. In this manner, the system costs are further reduced and the measuring unit can be further compacted in size. The elimination of a lens at the light source also eliminates undesired lens defects and their consequent variations in light output from LED to LED, thus increasing the measurement accuracy of the system of the present invention.

The system 10 for measuring the quality of a fluid further includes an electronics section 50 with a printed circuit board (PCB) 52. The optical sensor module 16 is mounted on the PCB, as well as the light source 12 and other components such as a processor 54 and a signal conditioning module 56 connected to the processor for driving a display (not shown), an audible signal device (not shown), and so on, based on signals from the processor. The processor can include means, such as software, circuitry, various electronic components, and so on, to process and analyze the captured digital image and determine one or more parameters of the fluid being measured based on the captured image. Data reflective of the liquid parameter(s) can be stored in a memory device and retrieved for signaling to a user, such as an operator, warranty entity, manufacturer, owner, fleet company, and so on, to indicate whether or not the proper DEF fluid has been put in the reservoir, and thus who may be at fault should a failure occur in the catalytic converter or other system components of the vehicle or diesel-powered equipment due to the use of improper fluid. Such data can also have a time/date stamp associated therewith to pinpoint the moment the improper fluid was added and/or used in the system, and thus who may be at fault when failure of one or more system components occurs.

It will be understood that data can be gathered in a similar manner, stored, and retrieved to indicate whether or not other automotive-type fluids (besides DEF) associated with vehicles or machinery, such as fuel, oil, windshield washer fluid, antifreeze, brake fluid, transmission fluid, and so on, are or were inside or outside of specified parameters or quality when first produced and/or introduced into the vehicle, machine, or other system. Thus, capturing data and warning an operator of potential catastrophic damage, as well as recording the introduction of improper fluids for determining who's at fault under warranty and/or repair situations, are made possible by the system 10 of the invention. It will be further understood that the present invention can be applied to non-automotive fluids, such as processing fluids, medical industry fluids, beverages, and so on, without departing from the spirit and scope of the invention.

Figure 5:
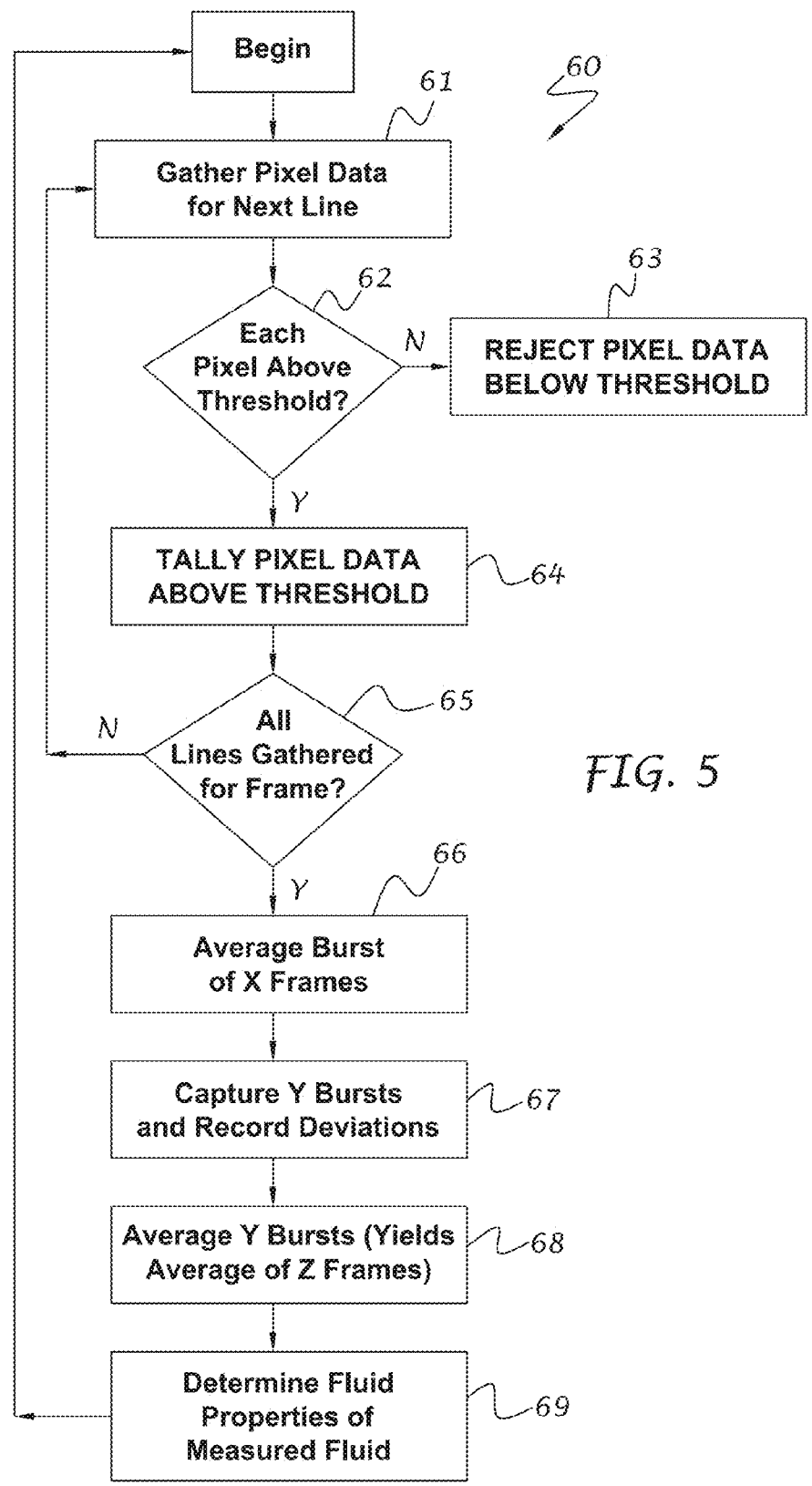
FIG. 5 is an exemplary algorithm for measuring and capturing sensor data related to the measurement system in accordance with the invention.

Referring now to FIGS. 3-5, a method 60 for processing data gathered by the optical sensor module 16 is illustrated. The method 60 includes first taking a snapshot or frame of the image projected onto the image surface 34 or the image as seen at the area 32 (FIGS. 1 and 2). The snapshot can be taken by gathering pixel data for each line of a frame (block 61), which can include a predefined area, the entire area, or a dynamically determined area of the optical sensor module 16. Each line of pixel data is then analyzed at block 62 to determine if each pixel is above a predetermined or dynamically determined brightness threshold. For example, in the exemplary embodiment having an optical sensor module in the form of a CMOS monochrome digital image sensor chip with a resolution of 640 by 480 pixels with each pixel capable of distinguishing and capturing 256 levels of visible light, the predetermined brightness threshold may be set at level 120. It will be understood, of course, that the brightness level threshold for the exemplary embodiment can be set in the range from 1 to 256 depending on the particular parameters of the optics and the fluid being measured. If, in block 62 the pixel value is below the predetermined brightness threshold value, it is discarded at block 63. The term "discarded" as used herein can mean that the pixels that fall below the predetermined value are held or stored in memory or storage, but not used for the present processing method, or that the pixel values are erased from memory or storage. If the rejected pixels are held in memory or storage, they may be subsequently used in further processing methods to determine further information, such as image shifting where the amount of shifting is a function of the refractive index of the fluid being measured, or other characteristics of the fluid being measured. At block 64, the pixel data for all pixels with a brightness value at or above the predetermined brightness threshold for the line of pixels just gathered is added. At block 65, it is determined whether or not all lines from the entire frame or predefined area(s) therefrom have been gathered. If not, the next line of pixel data is gathered at block 61. If all lines of the frame or frame portion have been gathered and tallied, then an average brightness value of the frame or frame portion is calculated. This process is repeated until the average brightness values of a predetermined number of frames or frame portions have been obtained. It will be understood that all data may be gathered then tallied together rather than tallying each separate line as described above. However, the single line method is preferred as it increases processing speed and preserves processor memory. At block 66, a predetermined number of frames are averaged, such as eight frames for example, after excluding the first frame, which may not have good data integrity. At block 67, a predetermined number of bursts (each burst representing the predetermined number of frames) are captured, such as four bursts for example, and the deviations of the four bursts are recorded. At block 68, the predetermined number of bursts (in this example four bursts) are averaged to thereby yield an average of 32 frames, for example, when eight frames are included in each burst. This step can be completed over a time interval of several milliseconds then repeated again for subsequent measurements. In this manner, a total pixel brightness value or pixel count value can be registered and used to a high degree of accuracy to determine whether or not the fluid being measured falls within acceptable parameters, as shown at block 69. It will be understood that more or less lines, frames, and/or bursts can be used without departing from the spirit and scope of the invention. It will be further understood that a pixel count, i.e. the number of pixels above the brightness threshold value, can be used in addition or alternatively to determine the fluid properties.

It will be understood that other processing techniques can be used in addition or alternatively to the above-described techniques. In particular, an area of pixels that are above (or below) the threshold value can be analyzed to determine further fluid properties. In addition, the light source 12 can include radiant energy at various wavelengths to obtain a spectral pattern for a particular fluid and determine its properties.

The techniques and methods discussed herein and as defined by the appended claims can be implemented in digital electronic circuitry, or in computer hardware, firmware, software, or combinations thereof. Apparatus may be implemented in a computer program product tangibly embodied in a machine-readable storage device for execution by a programmable processor; and the methods described herein may be performed by a programmable processor executing a program of instructions to perform functions by operating on input data and generating output. Further embodiments may advantageously be implemented in one or more computer programs that are executable on a programmable system including at least one programmable processor coupled to receive data and instructions from and transmit data and instructions to a data storage system, at least one input device, and at least one output device. Each computer program may be implemented in a high level procedural or object-oriented programming language, or in assembly or machine language, which can be compiled or interpreted. Suitable processors include, by way of example, both general and special purpose microprocessors. Generally, a processor receives instructions and data from read-only memory and/or RAM. Storage devices suitable for tangibly embodying computer program instructions and data include all forms of non-volatile memory including, by way of example and not by limitation, semiconductor memory devices, such as EPROM, EEPROM, and flash memory devices; magnetic disks such as internal hard disks and removable disks; magneto-optical disks; CD-ROM disks; solid state drives, and so on. Any of the foregoing may be supplemented by, or incorporated in, specially designed application specific integrated circuits (ASICs).

Figure 7:
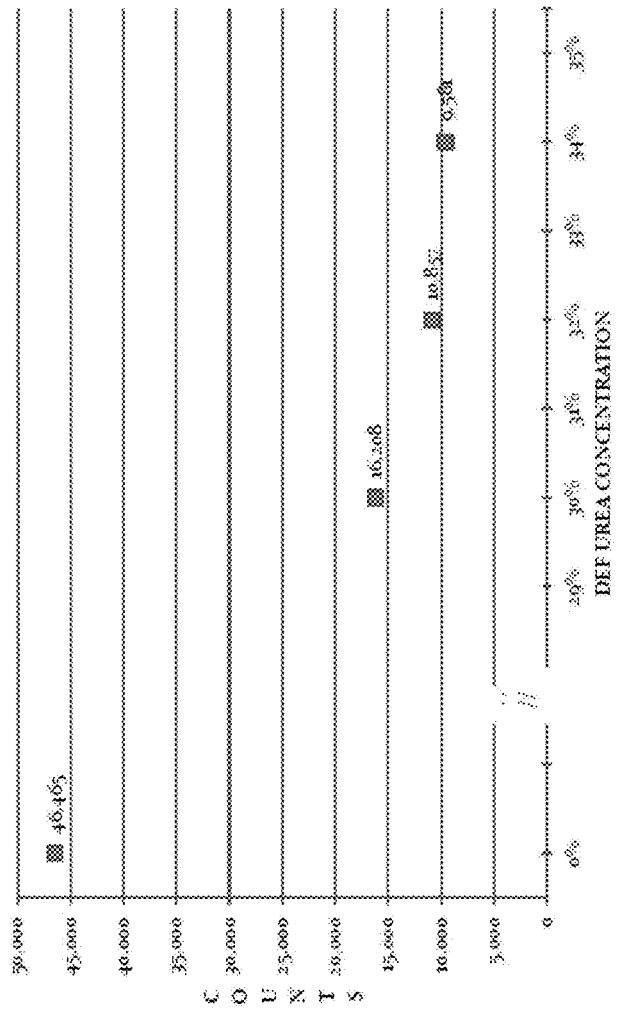
FIG. 7 is a graph showing the sensor data of FIG. 6.

Turning now to FIGS. 6 and 7, reflection information, in the form of pixel counts above the threshold brightness value were obtained during actual measurements using the setup of FIGS. 3 and 4. In particular, it was found that deionized water had 46,465 pixels above the threshold value. Likewise, it was determined that diesel exhaust fluid (DEF) having a solution of 30% laboratory grade urea in distilled water had 16,208 pixels above the threshold value. A difference between the pixel counts of the deionized water and 30% DEF solution was 34,257. Accordingly, deionized water was easily distinguishable from the 30% DEF solution. In addition, it was determined that DEF having a solution of 32% laboratory grade urea in distilled water had 10,857 pixels above the threshold value. A difference between the pixel counts of the 30% DEF solution and 32% DEF solution was 5,351. Likewise, it was determined that DEF having a solution of 33.9% laboratory grade urea in distilled water had 9,581 pixels above the threshold value. A difference between the pixel counts of the 32% DEF solution and 33.9% DEF solution was 1,278. This was accomplished using an optical sensor module having a 640 by 480 sensor (pixel) array. It has been found that much larger differences are achieved with higher resolution optical sensor modules, as will be described in greater detail below.

Figure 8:
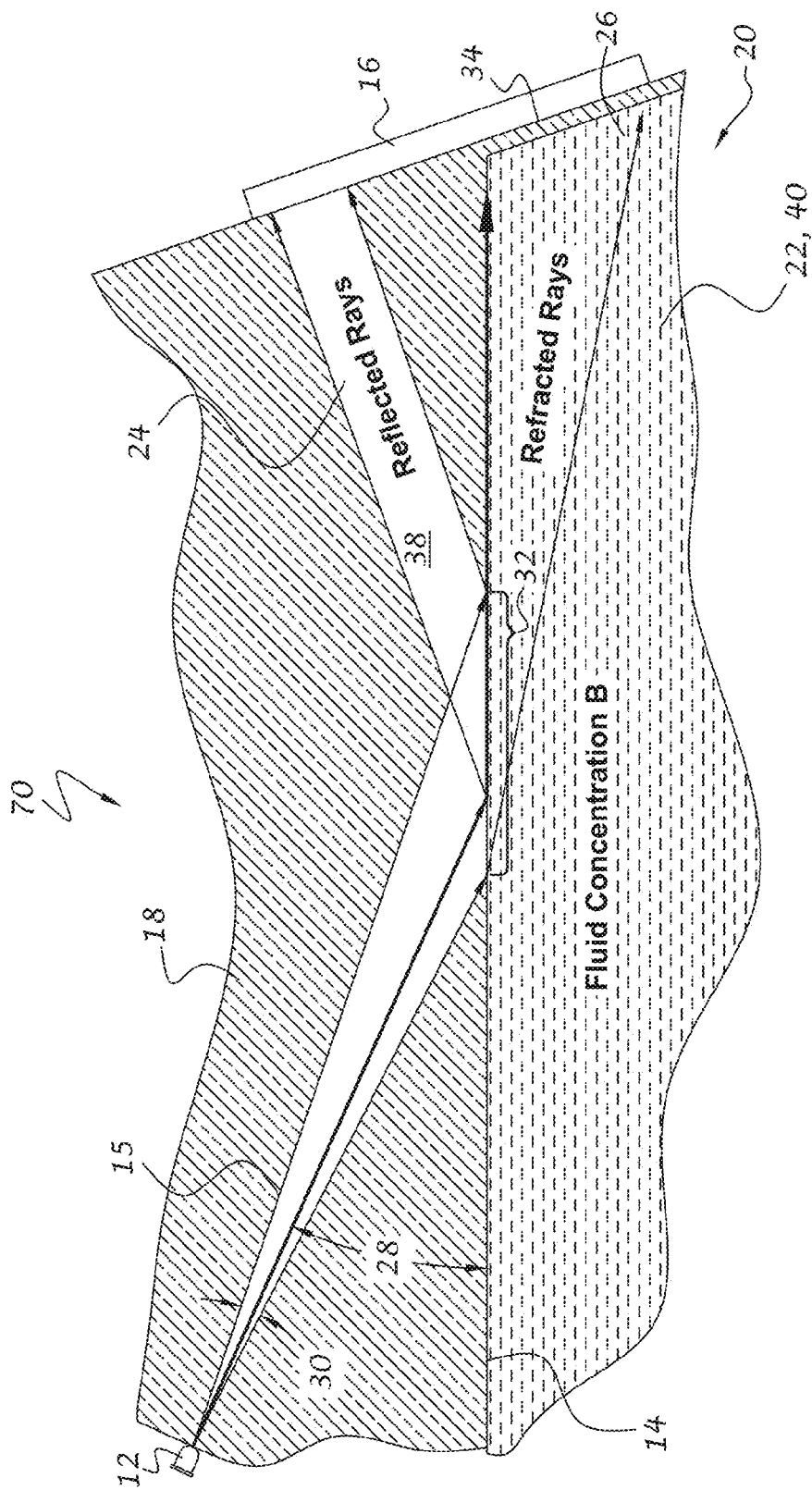
FIG. 8 is a diagrammatic view of a measurement system in accordance with the FIG. 4 embodiment to obtain reflection and refraction (absorption) data.

Referring now to FIG. 8, a system 70 for measuring the quality of a fluid, as well as other parameters, in accordance with a further embodiment of the present invention is illustrated. The system 70 is similar in construction to the system 10 previously described, with the exception that the optical sensor module 16 is shifted along the image surface 34 to obtain data related to both the reflected rays 24 traveling through the optical body 18 and the refracted rays 26 traveling through the fluid being analyzed, such as fluid 22 or fluid 40

(FIGS. 1 and 2). As in the previous embodiment, the pixel count is obtained, but this time for the pixels whose brightness value is above one or more predetermined or dynamic threshold brightness values. For example, the threshold value of the reflected rays may be the same or different from the threshold value of the refracted rays. As in the previous embodiment, it will be understood that other processing techniques can be used in addition or alternatively to the above-described technique of the present invention. For example, one or more areas of pixels that are above the threshold value can be analyzed to determine further fluid properties. In addition, the light source 12 can include radiant energy at various wavelengths to obtain a spectral pattern of both reflective and refractive rays for a particular fluid and determine its properties.

Figure 10:
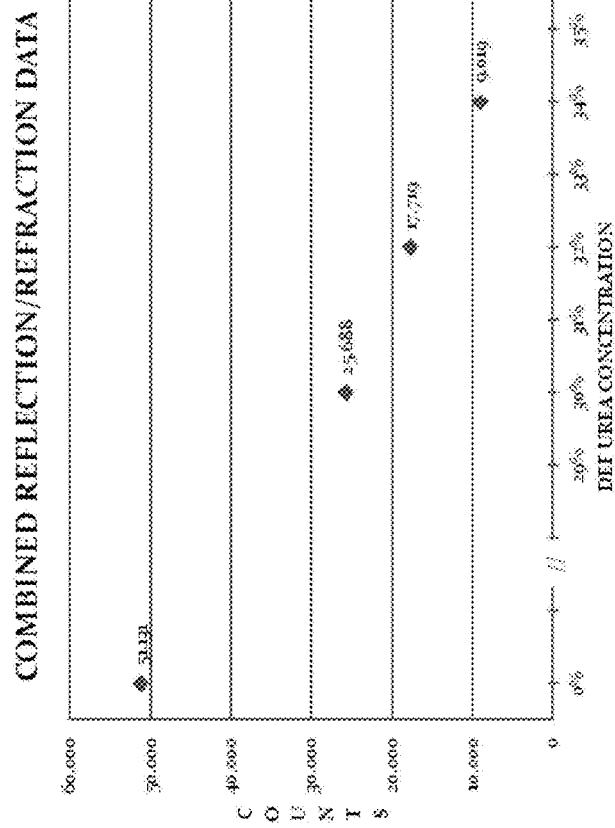
FIG. 10 is a graph showing the sensor data of FIG. 9.

Turning now to FIGS. 9 and 10, both reflection and refraction information, in the form of pixel counts above the threshold brightness value were obtained during actual measurements using the setup of FIGS. 3 and 4, but with the optical sensor module 16 shifted as shown in FIG. 8. In particular, it was found that deionized water had 51,131 pixels above the threshold value. Likewise, it was determined that DEF having a solution of 30% laboratory grade urea in distilled water had 25,688 pixels above the threshold value. A difference between the pixel counts of the deionized water and 30% DEF solution was 25,443. Accordingly, deionized water was easily distinguishable from the 30% DEF solution. In addition, it was determined that DEF having a solution of 32% laboratory grade urea in distilled water had 17,710 pixels above the threshold value. A difference between the pixel counts of the 30% DEF solution and 32% DEF solution was 7,969. Likewise, it was determined that DEF having a solution of 33.9% laboratory grade urea in distilled water had 9,019 pixels above the threshold value. A difference between the pixel counts of the 32% DEF solution and 33.9% DEF solution was 8,700. This was accomplished using the same optical sensor module having a 640 by 480 sensor array. Again, it has been found that much larger differences can be achieved with higher resolution optical sensor modules. From the graph shown in FIG. 10, it is apparent that the combined technique of detecting the pixel count for both reflected and refracted light rays produces a more linear output. Thus, the approximate difference of 8,000 pixels between two percentage points of the DEF concentration is both surprising and significant. In prior art devices and techniques, arriving at the capacity to distinguish between a single percentage in DEF concentration has been extremely difficult and, as far as the prior art is understood, has not been achieved until the present invention. Thus, in accordance with the present invention, a pixel count, and thus a measurement count, of approximately 4,000 points between a single percent change in DEF solution is now possible, giving a potential accuracy of measuring DEF down to 0.025% concentration using a 640×480 sensor array. This is a significant improvement over the greater than +/−2% accuracy of prior art solutions. Again, it has been confirmed that the use of sensor arrays with higher resolution in accordance with the invention has led to significantly greater accuracy of determining the fluid quality without a significant increase in cost. It will be understood that measurement of the Urea concentration in DEF is only one example as one or more parameters of virtually any fluid, combinations of fluids, semi-solids, and even solids can be measured with the fluid measuring systems as described herein without departing from the spirit and scope of the invention.

Figure 11:
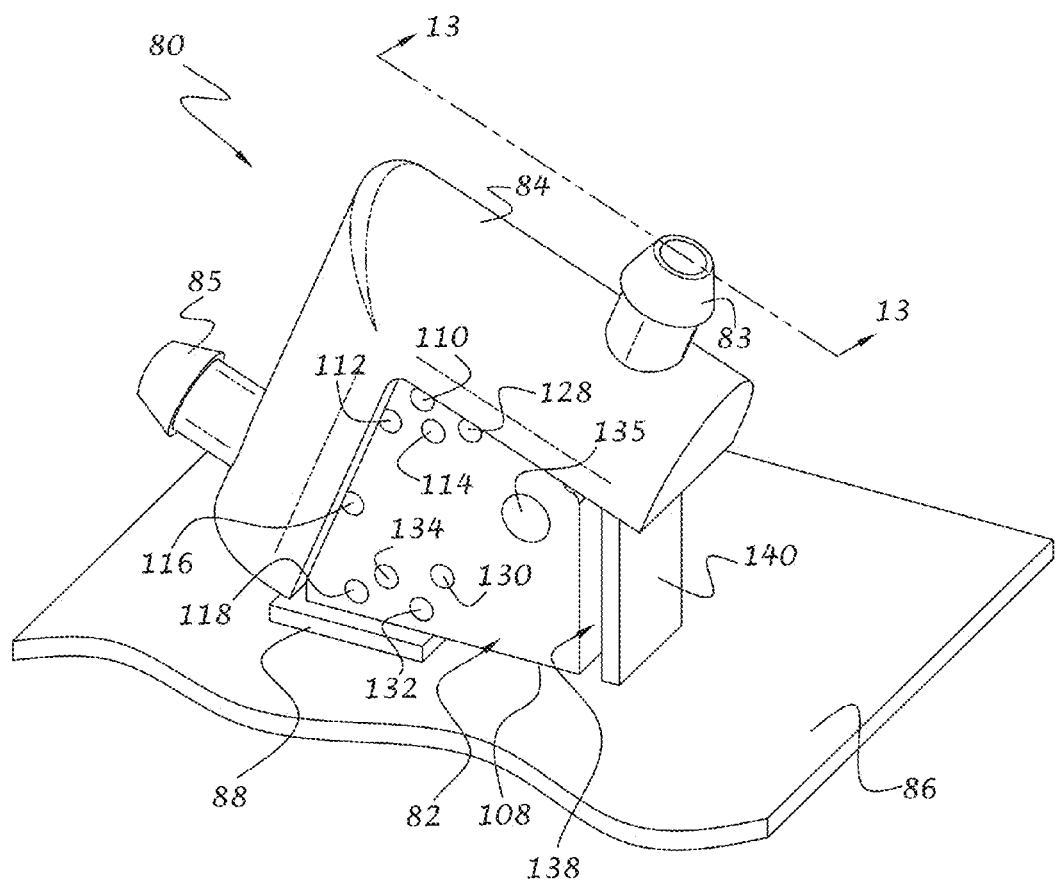
FIG. 11 is an isometric view of an exemplary measurement transducer assembly incorporating a sensor array in accordance with a further embodiment of the invention.
Figure 12:
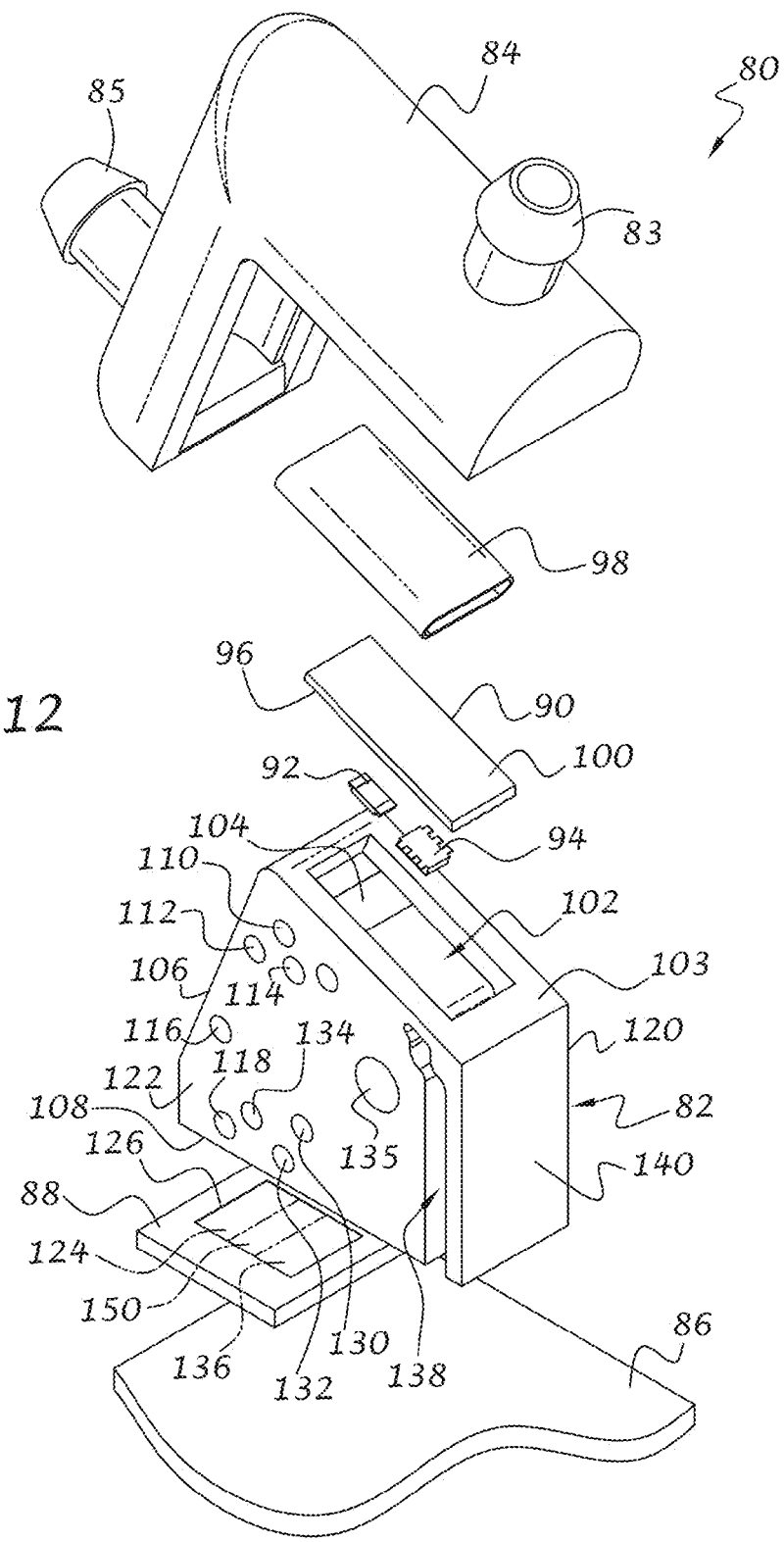
FIG. 12 is an exploded isometric view thereof.
Figure 13:
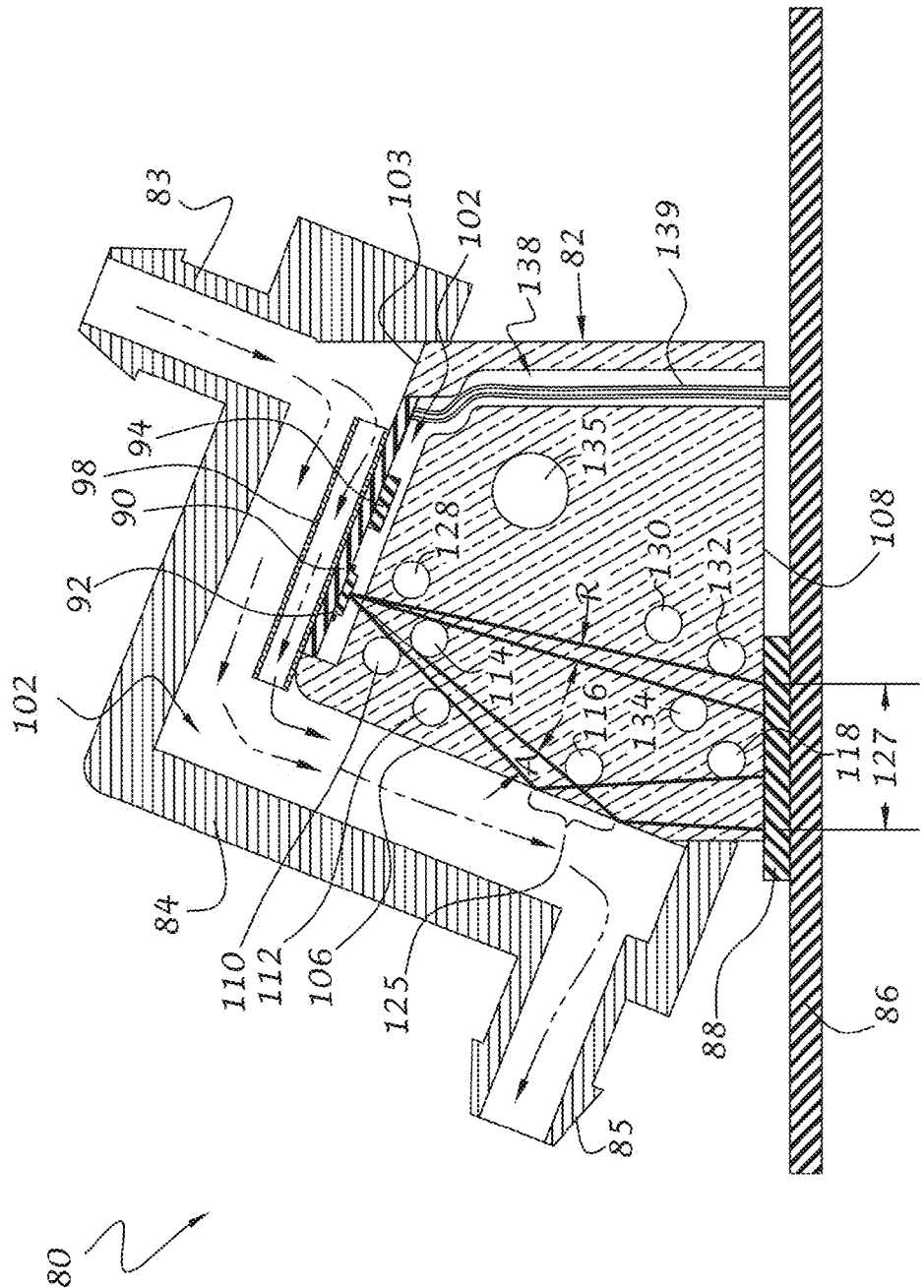
FIG. 13 is a sectional view of the transducer assembly taken along line 13-13 of FIG. 11 and diagrammatically showing light paths of a light source of the sensor assembly.

Referring now to FIGS. 11 to 13, a system 80 for measuring the quality of a fluid, as well as other parameters, in accordance with yet a further embodiment of the present invention is illustrated. The system 80 preferably includes an optical body 82 connected to a housing 84 that may be configured for inline, in-tank-, or in-tank-head measurement systems to thereby measure the quality and/or type of a fluid as it is being transferred from one location to another, such as for example from a DEF tank to a catalytic converter or other part of a SCR system; from a filling station to the DEF tank; from the DEF tank and back into the DEF tank, and so on. To that end, an input barb 83 and an output barb 85 can be associated with the housing 84 for connection of tubing or the like to transport the fluid to be measured through the housing 84 and across the optical body 82. As in the previous systems, it will be understood that one or more parameters of virtually any fluid, combinations of fluids, semi-solids, and even solids can be measured with the fluid measuring system described herein without departing from the spirit and scope of the invention.

The system 80 includes a primary PCB 86 with an optical sensor module 88 that is positioned with respect to the optical body 82 for determining various fluid parameters as described with the previous embodiments. The optical sensor module 88 can be a surface-mount device to save space and optically couple with the optical body without the need for lenses or other optical parts or optical assemblies. Other components associated with the PCB and the system 80 will be described with reference to FIG. 14 below.

As best shown in FIGS. 12 and 13, the system 80 further includes a secondary PCB 90 with a light source 92, such as a surface-mount LED, is connected to the bottom or inner surface 96 of the secondary PCB 90. A temperature sensor 94 is also mounted on the bottom surface 96 and a heat sink 98 is thermally connected to the top or outer surface 100 of the secondary PCB. The heat sink 98 is oval in shape, as shown in FIG. 12, but may be of any suitable shape and include cooling or radiating fins (not shown). The heat sink 92 is in a fluid flow path of the sealed interior 102 (FIG. 13) located between the optical body 82 and the housing 84 so that the temperature of the fluid to be measured is at least partially stabilized as it passed through and around the heat sink 92. The secondary PCB is preferably sufficiently thin so that differences in temperature between the outer and inner surfaces are minimized. In this manner, the temperature of the fluid to be measured can be ascertained to a high degree of accuracy, depending on the type of temperature sensor selected. The temperature sensor 94 may alternatively be mounted to the outer surface 100 to be in more direct contact with the fluid to be measured without departing from the spirit and scope of the invention.

A channel or conduit 138 is formed in the side surface 122 of the optical body 82 for receiving an electrical cable 139 to thereby electrically connect the secondary PCB 100 to the primary PCB 86. Although the channel 138 is open from the side surface 122, it will be understood that the channel can be a closed conduit and/or formed at other locations on the optical body 82 or outside of the optical body as long as the primary and secondary PCB's are electrically connected together. A hole 135 is formed in the optical body 82 and extends between the side surfaces 120 and 122. The hole 135 is sized to receive a threaded fastener or the like for mechanically connecting the optical body to housing structure. It will be understood that the hole 135 can be eliminated and that the optical body 182 can be connected to suitable structure through any well-known connection means such as adhesive bonding, clamping, fastening, ultrasonic welding, and so on.

The optical body 82 is preferably formed of transparent material, such as acrylic, polycarbonate, glass, or any other material that is transparent or translucent to the radiant energy emitted by the light source. The optical body 82 includes a channel 102 formed in a top surface 103 thereof for receiving the secondary PCB 90 and the attached LED 92 and temperature sensor 94. The LED 92 is set at a position on the secondary PCB 90 to be in alignment with a window 104 formed in the channel 102 so that radiant energy from the LED can be directed towards both a front measurement surface 106 and a bottom surface 108 which faces the optical sensor module 88. The particular angle between the measurement surface 106 and the bottom surface 108 can greatly vary depending on the fluids to be measured and the amount of accuracy desired when measuring subtle differences between similar fluids under varying atmospheric conditions and/or variations in the contents of the fluid. By way of example, for DEF fluids having a concentration of urea in deionized water ranging from about 30% to 35%, the measurement surface 106 extends at an angle of about 68.5 degrees with respect to the bottom surface 108. Surprisingly, it has been found that very high accuracy can be obtained for measuring differences in the relatively narrow range of DEF fluids when taken in conjunction with a predefined measurement cone angle of radiant energy emanating from the light source.

It will be understood that the measurement surface 106 is not limited to a flat profile at the particular angle as shown and described, but can be oriented at any suitable angle and may comprise other shapes include concave or convex surfaces, multifaceted measurement surfaces, combinations thereof and so on, without departing from the spirit and scope of the invention.

A plurality of light blocking apertures 110, 112, 114, 116, and 118 are formed at predefined locations in the optical body and extend between the right side 120 and left side 122 thereof to direct light from the LED 92 towards a transparent window 125 (FIG. 13) formed on the measurement surface 106 (best shown in FIG. 13) which is then reflected and/or refracted towards the bottom surface 108, and thus to a measurement sensor array area 124 (FIGS. 12 and 16) of a "frame" or sensor array portion 126 of the optical sensor module 88. The amount of reflected and/or refracted radiation is proportional to the refractive index of the fluid being measured, and thus can greatly vary even for similar fluid types.

Likewise, a plurality of light blocking apertures 128, 130, 132, and 134 are formed at predefined locations in the optical body 82 and extend between the right and left sides thereof to direct light, in conjunction with aperture 114, from the LED 92 towards the bottom surface 108, and thus to a reference sensor array area 136 (FIGS. 12 and 16) of the sensor array portion 126 of the optical sensor module 88. In this manner, the brightness of the light source can be constantly monitored by the reference sensor array area 136 which may be caused by changing atmospheric or environmental conditions, degradation of the light source over time, compensation for lower brightness when the power supply is in the form of a battery for portable measurement applications, and so on, so that any changes in the brightness of the light source measurement due to such conditions can be compensated for.

Preferably, the entire optical body 82, including the apertures 110, 112, 114, 116, 118, 128, 130, 132, and 134, as well as the hole 135, top surface 103, top channel 102, measurement surface 106, bottom surface 108, side surfaces 120 and 122, the rear surface 140, and the side channel 138 of the optical body 82 are coated with a dark layer of material such that radiant energy reaching the apertures, surfaces, and channels from the LED are at least substantially absorbed to prevent undesired radiant energy from reaching the sensor array portion 126 of the optical sensor module 88. The window 104 in the channel 102, as well as window 125 (FIG. 13) on the measurement surface and a window 127 (FIG. 13) on the bottom surface 108 are formed by masking off areas on those surfaces of the optical body 82 prior to coating. The coating preferably comprises a dark dye material that penetrates a short distance into the optical body. The coating can additionally or alternatively comprise dark paint or other materials that absorb undesirable light. Other coatings may also be used, including hydrophobic and/or oleophobic coatings, in order to reduce or eliminate contamination on the window areas of the optical body 82 that may otherwise be left by the fluid.

Since the preferred light source is a low-cost surface-mount LED without a lens (to avoid inaccuracies that may otherwise be introduced by variations in lens geometry of mass-produced LED's), the expanding radiant energy from the light source can be precisely controlled. For example, the thick lines 142, 144 in FIG. 13 represent a cone angle or otherwise divergent angle "A" of measurement light from the LED that is defined by the locations of the apertures 110, 114, 112, and 16, while a divergent reflective angle of the reflected light from the measurement surface 106 is controlled by the apertures 116 and 118. Likewise, a cone angle or otherwise divergent angle "R" of the reference light (represented by the thick lines 146 and 148 in FIG. 13) from the same LED can be precisely controlled by the locations of the apertures 128, 114, 130, and 134. By way of example, the diverging beam of the "active" or measurement light can have an active angle "A" of approximately +/−three degrees while the diverging beam of the "reference" light can have a reference angle "R" of approximately +/−five degrees. Thus, as in the previous embodiment, radiant energy projects onto the measurement surface at the predefined area so that the rays of light extend at angles less than, equal to, and greater than the critical angle (or converse to the critical angle) between the optical body and the fluid to be measured.

It will be understood that the angles of diverging light can greatly vary depending on the angle or inclination of the measurement surface 106 with respect to the bottom surface 108 and the particular fluid(s) to be measured. Accordingly, the diverging light spray from the LED that would otherwise extend over a relatively large angle, can be controlled without the radiant energy being directed through lenses, aperture plates, or other optical components, thereby reducing the number of parts, inaccuracies due to tolerance accumulations, and so on. However, it will be understood that such optical devices can be used in conjunction with the methods of the invention for determining one or more parameters of the fluid being measured.

It will be understood, that the apertures can be replaced with slots or other light directing features without departing from the spirit and scope of the invention. By way of example, the material between apertures 110 and 112 can be removed to form an elongate slot extending through the optical body 82. Likewise, the material between apertures 114, 116, 118, and 134 can be removed to form a triangular-shaped slot between the measurement light rays and the calibration light rays. It will be apparent that other slots can extend between other aligned apertures.

In accordance with one embodiment of the invention, where the ideal fluid 22 being measured is 32.5% laboratory grade urea in deionized water, the particular angle 28 is approximately equal to the critical angle (or the converse of the critical angle) as determined by a ratio of the refractive indices of the optical body 82 and the fluid to be measured. In addition, the light source 92 also projects radiant energy 15 at a cone angle 30 so that the radiant energy is distributed over a relatively large surface area 32 so that rays of light extend at angles less than, equal to, and greater than the critical angle (or converse to the critical angle). In this manner, a wide variety of different fluids, fluid combinations, semi-solids, and solids with different refractive indices can be measured.

With this arrangement, lenses, mirrors, and/or other optical components are not needed, thus significantly reducing the number of parts, assembly time and other manufacturing costs, as well as their associated drawbacks (such as condensation, parallax errors, inherent defects in low-cost lenses, lens systems, mirrors, and so on). However, it will be understood that real image data can be captured and processed using one or more lenses and/or lens systems, mirrors, and other optical elements for analyzing the fluid in accordance with the measurement methods of the invention. Regardless of the manner in which the image data is created (e.g. either real or virtual image creation), it will be understood that the image data can be processed in a similar manner to determine the fluid quality, as discussed above with respect to FIG. 5 and as will be discussed below with reference to FIG. 15.

The optical sensor module 88, as in the previous embodiment, is preferably in the form of a two-dimensional image sensor, such as a digital image module. The digital image module is preferably of a relatively low-cost variety, having a particular number of pixels or independent sensors, commonly used in other mass-produced applications such as smart devices, mobile phones, touch pads, digital cameras, and so on. A suitable image module may include, but is not limited to, a CMOS image sensor with a predetermined array of light sensitive sensors or pixels to capture an image of the measurement surface area as defined by the measurement window 125. The sensor array portion 126 preferably includes a dark or calibration sensor array area 150 (FIG. 16) located between the measurement sensor array area 120 and reference sensor array area 126. The dark sensor array area 150 is at least substantially void of light so that variations in signals from the third sensor array area are not affected by light but rather of the response of the sensor array portion 126 under varying conditions independent of light, such as such as temperature, pressure, humidity, and so on. Accordingly, errors produced by the optical sensor module 88 can be monitored and compensated for independent of variations in light that may be present at the first and second sensor array areas.

Figure 16:
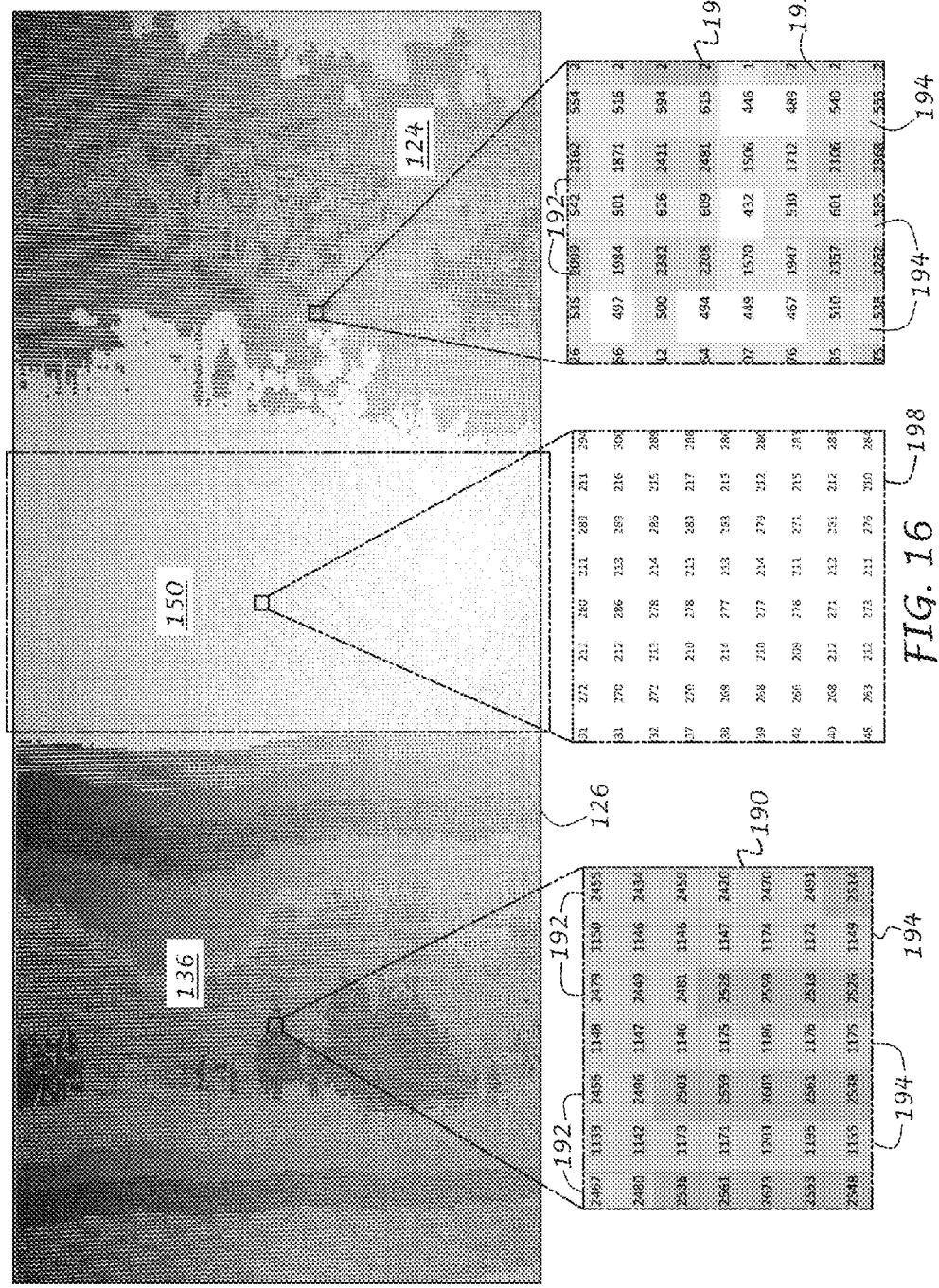
FIG. 16 shows actual data gathered by the measurement transducer of FIG. 11 and displayed in a spreadsheet wherein a value of each pixel and corresponding color assigned to a range of values are associated with separate cells of the spreadsheet in accordance with corresponding pixel locations in the sensor array.

In accordance with an exemplary embodiment of the invention, a 12-bit CMOS color digital image sensor chip was selected for the optical sensor module 88 and was used to collect the data as shown in FIG. 16. The exemplary digital image optical sensor module has a resolution of 5 megapixels with a matrix of 2,592×1,944 pixels. Each pixel is capable of distinguishing between 4,096 different brightness levels of visible light. The matrix of pixels can follow a Bayer pattern with alternating rows of green and red pixels and blue and green pixels. The digital image sensor is also capable of operation at 15 frames per second (fps) in full resolution. A suitable digital image sensor that meets this configuration is known at the MT9P004 by Aptina™. However, it will be understood that the particular digital image sensor can vary greatly in resolution, may have lower or higher detection levels of brightness, and may have other configurations or patterns of red, blue and green pixels. It will be further understood that the digital image sensor can be a monochrome device, as discussed in the previous embodiment.

With the exemplary optical sensor module 88 having a resolution of 5 megapixels and 4,096 brightness levels per pixel, it was found that image data of the fluid being measured can be captured to a very high degree of resolution when compared to prior art devices, as will be described below with reference to FIG. 16. Accordingly, very high accuracy measurements have been obtained for determining the type and/or quality of the measured fluid when compared with prior art solutions. As in the previous embodiment, the data captured during imaging can be transferred by any available data format such as a standard parallel digital video port (DVP) or by a single-lane MIPI high-speed serial interface with RAW pixel data, RGB, YUV, and/or Compressed Data outputs.

Figure 14:
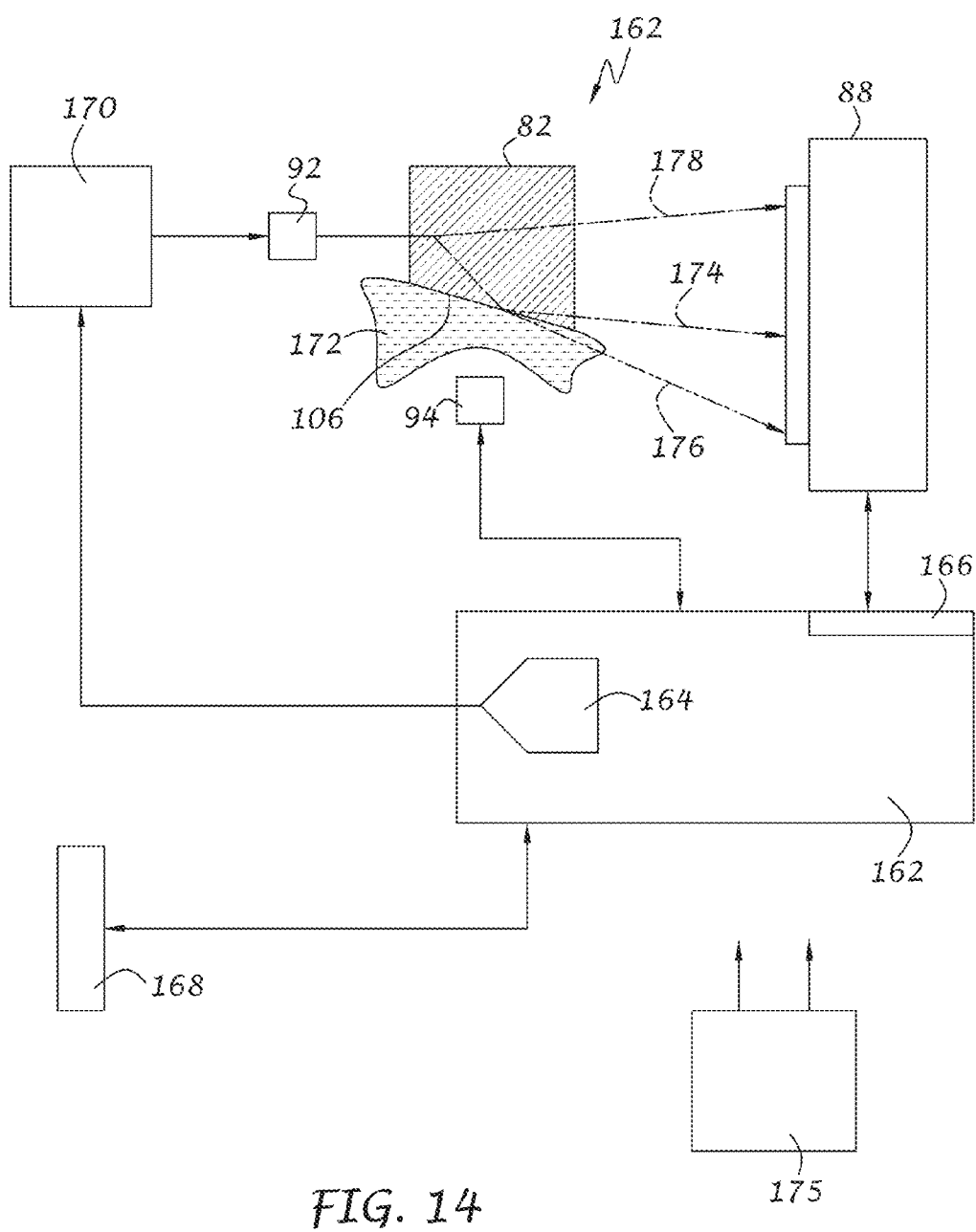
FIG. 14 is an exemplary block diagram of basic electronic and optical components of the transducer assemblies of the present invention.

As shown in FIG. 14, a block diagram 160 of basic electronic and optical components of the fluid measurement systems of the invention is illustrated. The systems of the invention preferably include a processor 162, such as a microprocessor, with an integrated digital to analog converter (DAC) 164 and an integrated data interface 166 for receiving data from the digital image sensor chip 88. An external interface port 168 is connected to the processor 162 for transferring measurement data, alarm signals, display data, and so on, to a user interface to thereby communicate the quality of the fluid and/or the type of fluid being measured. An LED current driver 170 is connected between the DAC of the processor 162 and the LED 92 for controlling the brightness of the LED 92 under varying atmospheric conditions through a closed-loop feedback system where the LED brightness is monitored by the reference sensor array area 136 (FIG. 16) and optionally temperature data that is received from the temperature sensor 94. In this manner, the LED brightness can be precisely controlled by changing the amount of current flowing through the LED so that a steady brightness of light is directed toward the measurement surface 106, thus contributing to greater accuracy of the fluid measurement system independent of fluid temperature and other atmospheric conditions. The temperature sensor 94 is connected to the processor 162 for measuring the temperature of the fluid 172 to be measured. The selection of a particular temperature sensor 94 will largely depend on the desired accuracy of the fluid measurement, as temperature can affect the properties of the fluid. Thus, a temperature sensor with relatively high accuracy will result in a fluid measurement of higher accuracy since compensation of the brightness of the light source, and thus the fluid properties, is possible with a more precise temperature reading. A power source 175 is electrically connected to the processor 162 and other active components, such as the LED 92 and sensor 88. The power source can be in the form of one or more batteries or other DC power source, or from an AC power source. For a portable unit used to measure the quality of type of fluid within a tank or container, the fluid measurement system may have one or more replaceable or rechargeable batteries.

The optical body 82, as previously described, optically interfaces between the LED 92, the fluid 172 being measured, and the digital image sensor chip 88. The measurement surface 106 is in contact with the fluid 172 at a particular cone angle such that some of the light is reflected towards the sensor 88, as represented by arrow 174, while some of the light can be refracted through the fluid 172, as previously described, toward the sensor 88, as represented by arrow 176. Likewise, a calibration portion of the light, as represented by arrow 178, travels through the optical block and towards the sensor 88 to compensate for variations in LED brightness due to temperature and other environmental factors. Although not shown, the bottom surface 108 can be lengthened and the optical sensor module 88 can be shifted to also or alternatively measure absorption characteristics of the fluid, as in the previous embodiment described above.

Figure 15:
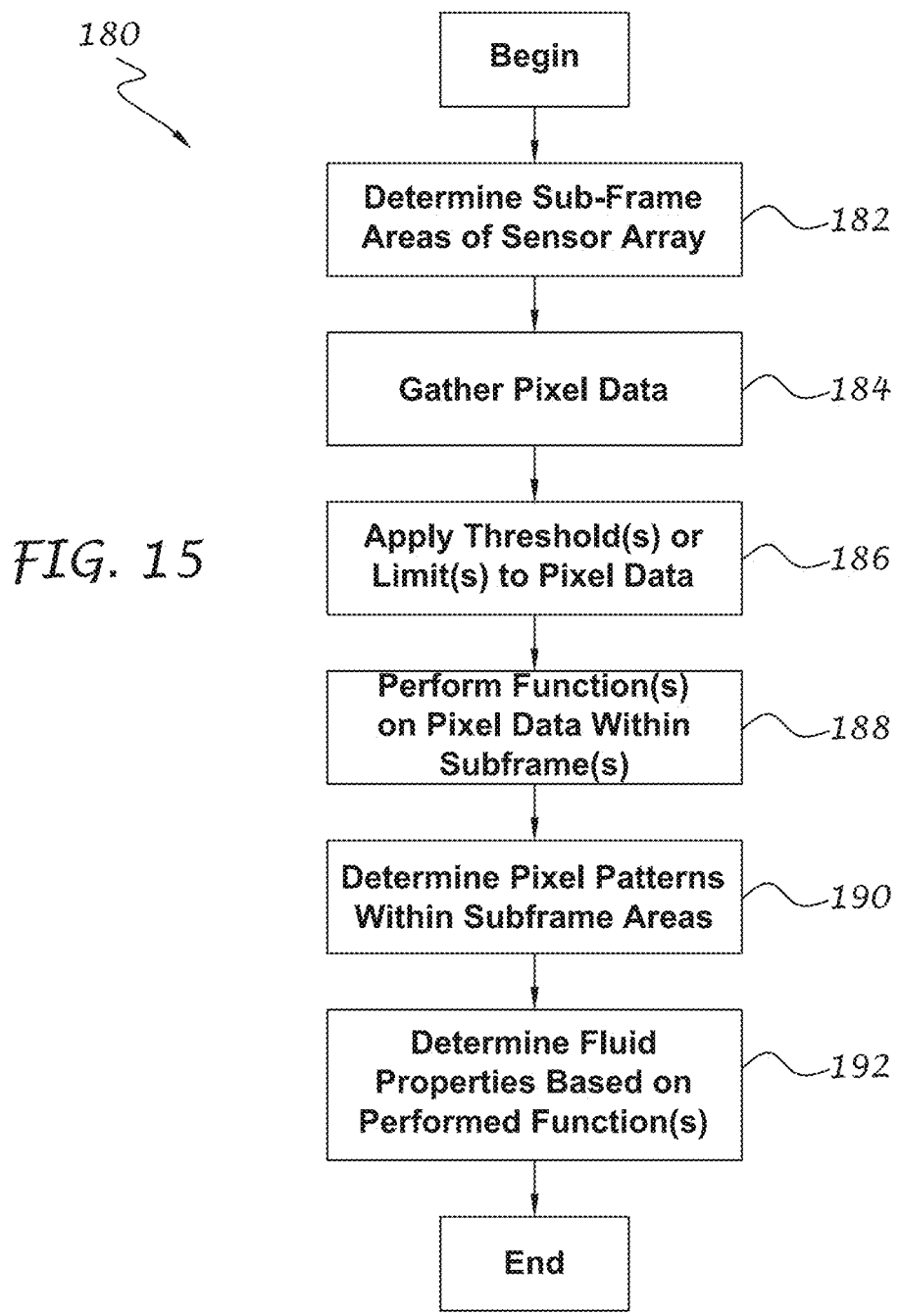
FIG. 15 is an exemplary algorithm for measuring and capturing sensor data related to the measurement systems in accordance with the invention.

Referring now to FIGS. 15 and 16, a method 180 for processing data gathered by the optical sensor module 88 is illustrated. The method 180 is similar in some respects to the method 60 previously described, and includes, as shown at block 182, dividing the image area 126 of the optical sensor module 88 into a measurement sensor array area 124, a reference sensor array area 136, and a calibration area array 150. As described above, the dark or calibration sensor array area 150 is located between the measurement sensor array area 120 and reference sensor array area 126 but may be eliminated when the optical sensor module 88 has integrated "dark" pixels that are never exposed to radiant energy for calibrating the response of the optical sensor module under varying atmospheric conditions independent of variations in radiant energy.

At block 184, the pixel data is gathered. Again, this can be accomplished by gathering pixel data for each line of a frame (image area 126), which can include one or more of the predefined measurement, reference, and calibration areas or portions thereof, the entire area, or a dynamically determined area of the optical sensor module 88. One or more brightness threshold(s) or limit(s) are then applied to the pixel data at block 186 to determine if each pixel is above a predetermined or dynamically determined brightness threshold. For example, in the exemplary embodiment having an optical sensor module in the form of a CMOS color digital image sensor chip with a resolution of 5 megapixels with each pixel capable of distinguishing and capturing 4,096 brightness levels of visible light, the predetermined brightness threshold may be set at level 2,500 for example. It will be understood, of course, that the brightness level threshold for the exemplary embodiment can be set in the range from 1 to 4,096 and may vary, either statically or dynamically, with each sensor array area depending on the particular parameters of the optics and the fluid being measured.

The information gathered from the image area 126 includes pixel brightness and pixel location within each of the predefined reference 136, measurement 124, and calibration 125 areas. At block 188, various functions can be performed on the pixel data including summing pixels above and/or below the predetermined or dynamic threshold, performing a normalization routine between the measurement and reference sensor array areas, and so on. When summing the pixels, the number of pixels above the brightness threshold can be counted, the value of the pixels above the brightness threshold can be added, the number of pixels below the threshold can be added, the value of each pixel below the threshold can be added, and/or the values of the pixels for the entire reference or measurement area can be added without setting the threshold. Other functions can include adding and/or averaging the data from multiple readings of the image area 126, which provides increased magnitude in resolution of the signal strength. At block 190, the shift of data patterns relative to previously gathered or recorded image areas can also be used as an identifier of change in fluid characteristics. Since, according to the exemplary embodiment, each pixel may have a brightness magnitude of 4,096 brightness levels. The under/over threshold and over/under limit characteristics can be utilized to include or exclude the data from each pixel within the totals or averages. Accordingly, one or more of the above-described functions can be used to determine one or more fluid properties or characteristics at block 192. A change of fluid characteristics, such as concentration, will cause a change of signal magnitude as well as a change of pixel signal concentration location within the measurement and reference sensor array areas. Identifying this shift in signal concentration can be utilized to identify additional characteristics of the fluid being measured.

Referring now to FIG. 16, an illustration of actual data gathered for a particular concentration of urea in deionized water with the exemplary optical sensor module 88 is shown. The data was imported into a spreadsheet with each cell representing a different pixel. Color values were assigned to each cell according to ranges of brightness within the 4,096 brightness levels. It was found that the pattern in the reference area 136, where the light from the LED is projected directly onto the reference area, remained substantially consistent from frame to frame and for different fluid concentrations.

The measurement area 124 on the other hand changed dramatically even within the small range of urea concentrations of about 30.5% to about 34.5% which, until the present invention, in-line or in-tank DEF quality transducers were only capable of measuring +/−2% concentration from the recommended 32.5% urea concentration. The calibration area 150 also remained constant throughout subsequent frames 126 of the module 88. As shown in the enlarged portion 190 of the reference area 136, each cell of the spreadsheet is associated with a different brightness level or value. Since the optical sensor module 88 in the exemplary embodiment follows the standardized Bayer pattern with alternating rows 192 and 194 (or columns depending on the module orientation) of green and red pixels and blue and green pixels, respectively. The light source 92 used in the exemplary embodiment was a red LED at a wavelength of approximately 680 nanometers. Thus, for the alternating rows 192 where the green and red pixels are located, the values are generally much higher than the rows where the blue and green pixels are located. Similar results were found for the measurement or "active" area 124 where an enlarged block 196 shows higher values in rows 192 than in rows 194. As shown, the active area 124 is quite distinguishable from the reference area 136 and may vastly change depending on the properties of the fluid being measured.

Likewise, the calibration area 150 with an enlarged block 198 to show the cell details, has values that are substantially lower than the measurement and reference areas since it is in substantially total darkness. As stated earlier, a detected change in these values represents changes in the properties of the optical module 88 independent of radiant energy, which can be used to compensate for measurements of the other areas. For example, an average brightness value of the pixels in the area 150 can simply be subtracted from the average values of the pixels in the measurement and reference areas. Other mathematical or calibration functions can be used without departing from the spirit and scope of the invention.

Figure 17:
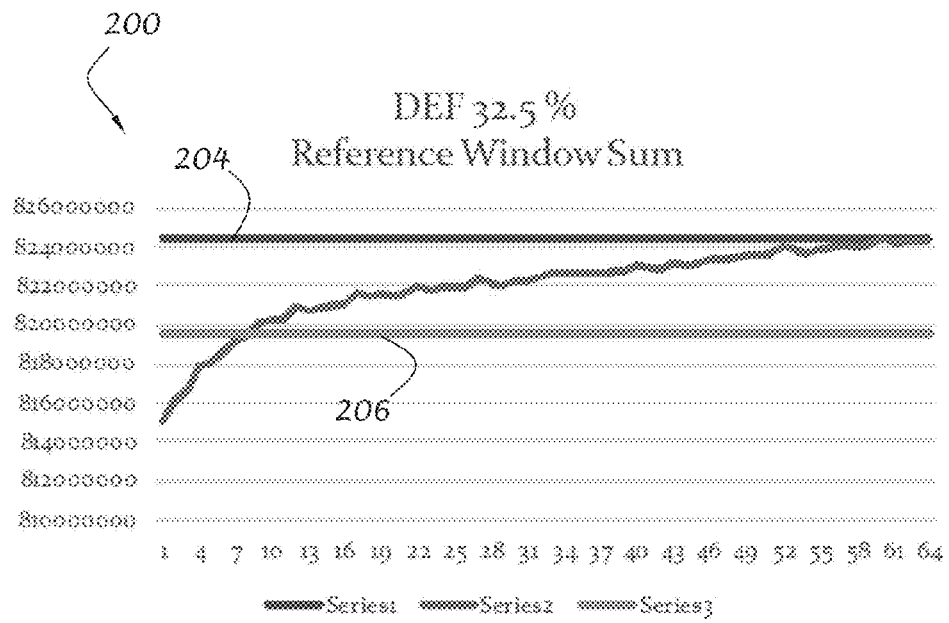
FIG. 17 is a chart plotting a summation of actual reference data of the light source as detected by a reference portion of a digital two-dimensional optical array taken over approximately one hour of time.
Figure 18:
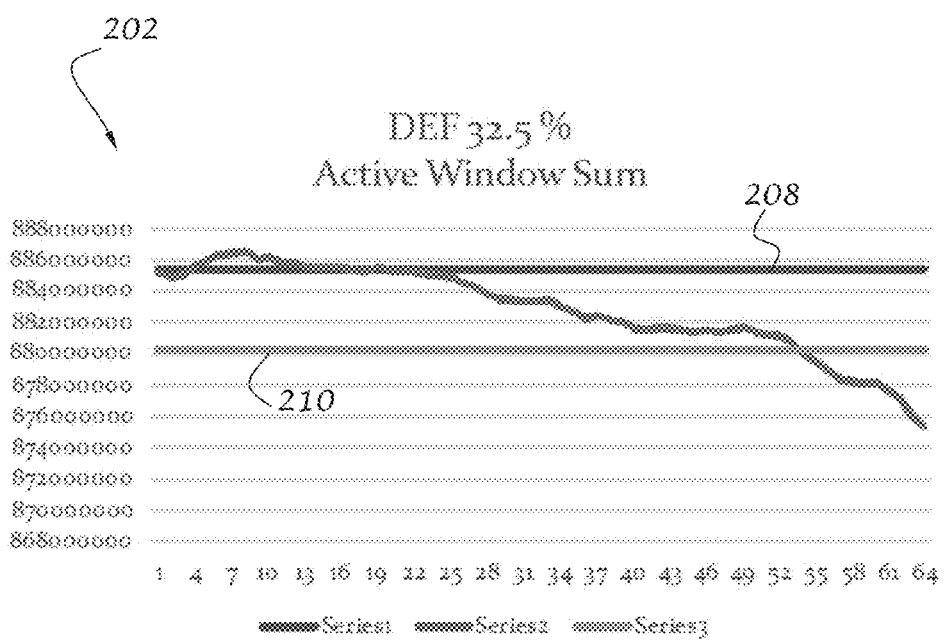
FIG. 18 is a chart plotting the summation of actual measurement data of DEF with a concentration of 32.5% urea in deionized water as detected by a measurement portion of the optical array over the same time interval as FIG. 17.
Figure 19:
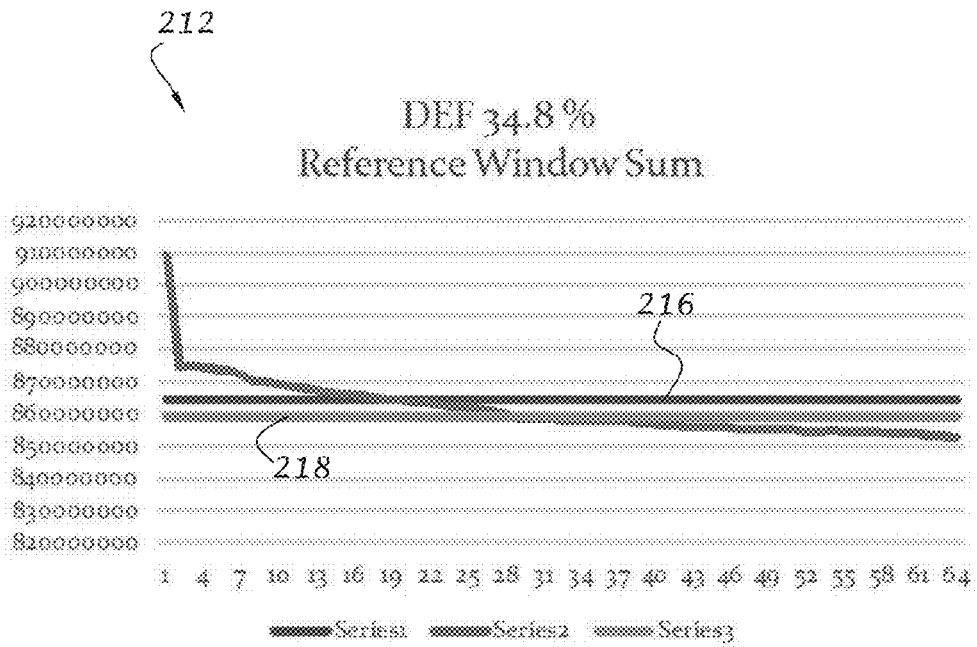
FIG. 19 is a chart plotting the summation of actual reference data of the light source under different measurement circumstances than FIG. 17, as detected by a reference portion of a digital two-dimensional optical array taken over approximately one hour of time.
Figure 20:
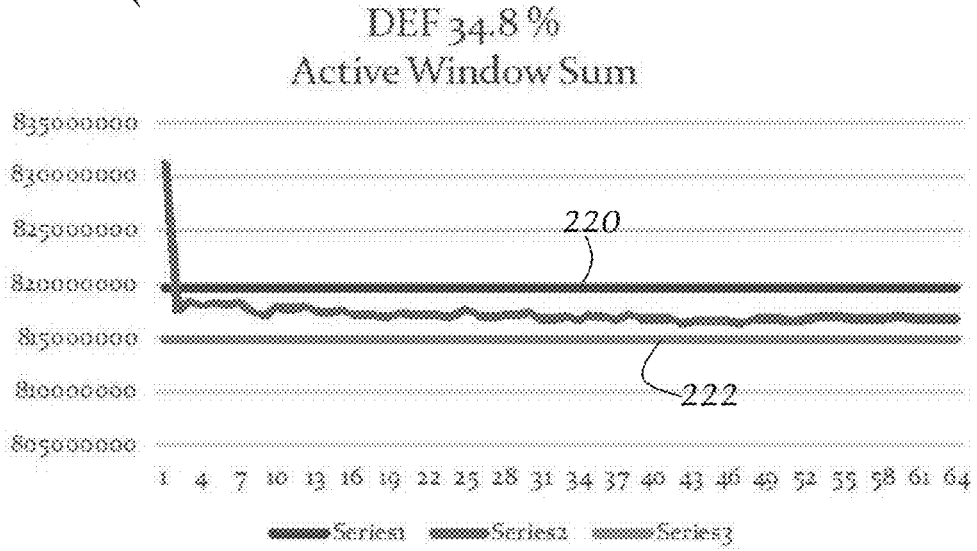
FIG. 20 is a chart plotting the summation of actual measurement data of DEF with a concentration of 34.8% urea in deionized water as detected by a measurement portion of the optical array over the same time interval as FIG. 17.

Referring now to FIGS. 17 and 18, a graph 200 of actual uncompensated data from the reference area 136 and a graph 202 of actual uncompensated data from the measurement area 124 are illustrated for DEF having a urea concentration of 32.5%. Each graph represents values of the brightness level in its associated area plotted over time (approximately one hour) while the DEF was flowing past the measurement surface to determine drift of the fluid in a stationary state. As shown in FIG. 17, an upper limit boundary 204 for the sum of the pixel values of the reference area is located at 824,000,000 and a lower limit boundary 206 thereof is located at 820,000,000. A substantial portion of the brightness in the reference area 136, over the 60-minute period, stayed within the upper and lower boundaries. The drift can most likely be attributed to separation of the fluid components while the fluid is stationary, i.e. not flowing across the optics. Likewise, as shown in FIG. 18, an upper limit boundary 208 for the sum of the pixel values in the measurement area is located at a value of 886,000,000 and a lower limit boundary 210 is located at a value of 880,000,000. A substantial portion of the average brightness in the reference area 136, once stabilized, over the 60-minute period, stayed within the upper and lower boundaries Referring now to FIGS. 19 and 20, a graph 212 of actual uncompensated data from the reference area 136 and a graph 214 of actual uncompensated data from the measurement area 124 are illustrated for DEF having a urea concentration of 34.8%. Each graph represents an average value of the brightness level in its associated area plotted over time (approximately one hour) to determine drift of the fluid in a stationary state. As shown in FIG. 19, an upper limit boundary 216 for the sum of the pixel values of the reference area is located at 860,000,000 and a lower limit boundary 218 thereof is located at about 865,000,000. A substantial portion of the average brightness in the reference area 136, over the 60-minute period, stayed within the upper and lower boundaries. Again, the drift can most likely be attributed to separation of the fluid components. Likewise, as shown in FIG. 18, an upper limit boundary 220 for the sum of the pixel values in the measurement area is located at a value of 820,000,000 and a lower limit boundary 222 is located at a value of 815,000,000. A substantial portion of the average brightness in the reference area 136, once stabilized, over the 60-minute period, stayed within the upper and lower boundaries. Due the very narrow band range of the measured DEF concentrations above, a very high degree of accuracy for determining the concentration of urea in DEF. It has been calculated that the accuracy of the percent urea in deionized water can be determined at least within +/−0.002% or even greater accuracy. Accordingly, the present invention is a substantial improvement over prior art systems that have an accuracy of +/−2%, and yet can remain competitive in cost. The greatly increased accuracy in DEF concentration determination is especially advantageous for example in SCR systems where, even if the urea concentration of the DEF is not ideal, the DEF can be accurately metered into the SCR system based on feedback from the NOx sensor and the DEF concentration as measured by the present invention to thereby maximize the reduction of NOx emissions in practically real time while allowing wide variations in DEF concentrations.

It will be understood that measurement of the DEF and the particular results obtained are by way of example only, since it is anticipated that substantially any fluid (including but not limited to gases, liquids, and solutions) and solid materials can be measured through the systems and methods of the present invention.

It will be further understood that the invention can include different calibration and/or measurement techniques. In accordance with a further embodiment of the invention, the reference area may be eliminated and a substantial portion of the image area 126 can be used alternatively for measuring fluid parameters and variations in light and surface contaminants. This can take place by filling the space surrounding the measuring surface 106 of the optical body 82, taking a first reading in the image area, then emptying the space surrounding the measuring surface and taking a second reading in the image area. The second reading can then be subtracted from the first reading or the first and second readings may be used in a normalization routine to eliminate error caused by variations in LED intensity and surface contaminants. An exemplary normalization routine can include the following formula:

$$\frac{A-B}{A+B}$$

Where "A" represents the reading of the image area when the space is empty and "B" represents the reading of the image area when the space is full of liquid. In this manner, signal variations associated with environmental conditions will be part of the numerator and denominator, and thus cancel out. The above formula can also be used for normalizing the reading between separate measurement and reference areas of the optical sensor module.

It will be understood that the above-described embodiments can be permanently mounted on equipment or may be constructed as portable units for measuring the properties of a variety of different fluids within transport lines, tanks or containers, across many industries, by users, field technicians, maintenance workers, claims adjusters, and so on.

It will be understood that terms of orientation and/or position as used throughout the invention relate to relative rather than absolute orientations and/or positions.

It will be appreciated by those skilled in the art that changes could be made to the embodiments described above without departing from the broad inventive concept thereof. It will be understood, therefore, that this invention is not limited to the particular embodiments disclosed, but it is intended to cover modifications within the spirit and scope of the present invention as defined by the appended claims.

We claim:

1. A system for measuring one or more parameters of a fluid, the system comprising:
    an optical body having a measurement surface configured for contacting the fluid to be measured;
    a light source for projecting radiant energy toward the measurement surface at a predetermined angle;
    an optical sensor module arranged for detecting an image of at least reflected radiant energy from the measurement surface, the optical sensor module including a two-dimensional array of light sensors, each light sensor being capable of detecting a plurality of brightness levels; and
    a processor configured for setting a brightness threshold value and comparing the brightness threshold value to the brightness level of at least some of the light sensors;
    wherein the at least one parameter of the fluid is determined at least in part by counting the light sensors above and/or below the brightness threshold value.

2. A system according to claim 1, wherein the optical sensor module comprises a digital image sensor array with the plurality of light sensors arranged as a plurality of pixels.

3. A system according to claim 2, wherein the processor is configured to count the number of pixels above the brightness threshold value for determining a quality of the fluid.

4. A system according to claim 2, wherein the processor is configured to add a brightness value of each pixel above the brightness threshold for determining a quality of the fluid.

5. A system according to claim 2, wherein the optical sensor module comprises at least a measurement area having a first predetermined number of pixels for receiving at least the reflected radiant energy from the measurement surface, and a reference area having a second predetermined number of pixels for receiving radiant energy from the light source in the absence of the fluid being measured;
    wherein the processor is configured to determine the at least one parameter of the liquid by comparing the measurement area with the reference area.

6. A system according to claim 5, wherein the optical sensor module further comprises a calibration area having a third predetermined number of pixels located between the measurement area and the reference area that is substantially void of radiant energy, with the processor being configured to reduce or eliminate signal noise caused by atmospheric conditions independent of radiant energy.

7. A system according to claim 5, wherein the reference area and the measurement area occupy the same space, the processor being configured to collect brightness data from the space at alternate intervals when the fluid to be measured is absent from and present on the measurement surface such that signal error due to possible contaminants on the measurement surface can be compensated for.

8. A system according to claim 5, wherein the optical body comprises;
   a top surface for receiving the light source;
   the measurement surface extending from the top surface;
   a bottom surface extending from the measurement surface at a predetermined angle, the bottom surface being located at least proximal to the digital image sensor array;
   left and right side surfaces extending between the top, measurement and bottom surfaces; and
   a plurality of openings extending through the optical body between the left and right surfaces, the openings placed to divide the light source into at least a measurement component and a reference component, with the measurement component projecting toward the measurement surface to be reflected and/or refracted therefrom towards the measurement area of the optical sensor module, and the reference component being projected towards the bottom surface and the reference area of the optical sensor module.

9. A system according to claim 2 and further comprising a current driver for controlling a brightness of the light source, the light source and current driver being in a closed loop feedback system with one or more pixels of the reference area; and
   the processor being configured to change current flowing through the light source via the current driver when the one or more pixels of the reference area have detected a change in a brightness of the light source to thereby provide a steady brightness of light to the measurement surface independent of changes in ambient temperature.

10. A system according to claim 1, wherein the optical sensor module is located for measuring both reflection and refraction of the radiant energy with respect to the measurement surface.

11. An optical body for measuring one or more parameters of a fluid, the optical body comprising:
    a top surface adapted to receiving a light source;
    a measurement surface extending from the top surface for contacting the fluid to be measured;
    a bottom surface extending from the measurement surface at a predetermined angle, the bottom surface being adapted to receiving a digital image sensor array;
    left and right side surfaces extending between the top, measurement and bottom surfaces; and
    a plurality of openings extending through the optical body between the left and right surfaces, the openings placed to divide the light source into at least a measurement component of light and a reference component of light, with the measurement component of light projecting toward the measurement surface at a predefined angle to be reflected and/or refracted therefrom towards a first sensor area of the optical sensor module, and the reference component of light projecting towards the bottom surface and a second sensor area of the optical sensor module.

12. An optical body according to claim 11, and further comprising:
    a light absorbing coating covering a substantial portion of the optical body including the plurality of openings;
    a first window associated with the measuring surface for receiving the measurement component of light; and
    at least a second window associated with the bottom surface so that at least reflected light at the first window is directed through the second window and onto the first sensor area;
    wherein the first and second windows are void of the light absorbing coating.

13. An optical body according to claim 12, and further comprising a low surface energy coating at least on the first windows to reduce buildup of contaminants from the liquid being measured.

14. A method of determining at least one parameter of a fluid to be measured, the method comprising:
    providing an optical measurement surface for contacting the fluid to be measured;
    directing radiant energy toward the optical measurement surface at a predetermined angle such that at least a portion of the radiant energy is reflected and/or refracted off of the optical measurement surface;
    detecting a two-dimensional image of the reflected and/or refracted radiant energy from the measurement surface with a two-dimensional array of light sensors, each light sensor being capable of detecting a plurality of brightness levels of the reflected and/or refracted radiant energy;
    setting a brightness threshold value for at least some of the light sensors; and
    adding the light sensors above and/or below the brightness threshold value to thereby determine the at least one parameter of the fluid.

15. A method according to claim 14, wherein the two-dimensional array of light sensors comprises a digital image sensor array with the plurality of light sensors arranged as a plurality of pixels.

16. A method according to claim 15, wherein the step of adding the light sensors comprises counting the number of pixels above the brightness threshold value for determining the at least one parameter.

17. A method according to claim 15, wherein the step of adding the number of light sensors comprises adding a brightness value of each pixel above the brightness threshold for determining the at least one parameter.

18. A method according to claim 15, and further comprising:
    dividing the digital sensor array into a first measuring area having a first predetermined number of pixels for receiving at least the reflected and/or refracted radiant energy from the measurement surface, and into a reference area having a second predetermined number of pixels for receiving radiant energy from the light source in the absence of the fluid being measured; and
    comparing the measurement area with the reference area to determine the at least one parameter of the liquid.

19. A method according to claim 18, and further comprising:
    dividing the digital sensor array into a calibration area having a third predetermined number of pixels located between the measurement area and the reference area that is substantially void of radiant energy; and
    at least reducing signal noise from the digital sensor array in response to atmospheric conditions independent of radiant energy.

20. A method according to claim 14, wherein the detecting step comprises detecting the two-dimensional image of the reflected and refracted radiant energy from the measurement surface.

* * * * *